(12) United States Patent
Rucker

(10) Patent No.: US 8,148,409 B2
(45) Date of Patent: Apr. 3, 2012

(54) PHENATHRENONE COMPOUNDS, COMPOSITONS AND METHODS

(75) Inventor: Paul V. Rucker, Carlsbad, CA (US)

(73) Assignee: Pfizer Inc., New York, NY (US)

( * ) Notice: Subject to any disclaimer, the term of this patent is extended or adjusted under 35 U.S.C. 154(b) by 372 days.

(21) Appl. No.: 12/505,932

(22) Filed: Jul. 20, 2009

(65) Prior Publication Data

US 2010/0069444 A1 Mar. 18, 2010

Related U.S. Application Data

(60) Provisional application No. 61/084,095, filed on Jul. 28, 2008.

(51) Int. Cl.
C07D 213/72 (2006.01)
A61K 31/44 (2006.01)
(52) U.S. Cl. ........................................ 514/352; 546/285
(58) Field of Classification Search ................ None
See application file for complete search history.

(56) References Cited

U.S. PATENT DOCUMENTS

| 6,852,719 | B2 | 2/2005 | Liu et al. | |
|---|---|---|---|---|
| 7,547,714 | B2 * | 6/2009 | Cheng | 514/352 |
| 7,598,231 | B2 * | 10/2009 | Cheng et al. | 514/89 |
| 2002/0107235 | A1 | 8/2002 | Liu et al. | |

FOREIGN PATENT DOCUMENTS

| EP | 1201649 | 5/2002 |
|---|---|---|
| EP | 1201660 | 5/2002 |
| EP | 1201665 | 5/2002 |
| WO | WO00/66522 | 11/2000 |
| WO | WO2004/005229 | 1/2004 |
| WO | WO2006/078846 | 7/2006 |
| WO | WO2008/007149 | 1/2008 |
| WO | WO2008/064274 | 5/2008 |

OTHER PUBLICATIONS

J. Pharm. Sci., 1999; V88(10), pp. 955-958.

* cited by examiner

*Primary Examiner* — Zinna Northington Davis

(57) ABSTRACT

The present invention is directed to compounds of Formula I:

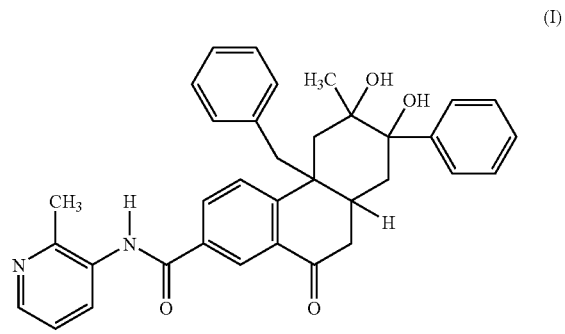

or salt thereof, which are modulators of the glucocorticoid receptor. The compounds and salts of the invention are useful in the treatment of conditions mediated by glucocorticoid receptor activity.

6 Claims, No Drawings

PHENATHRENONE COMPOUNDS, COMPOSITONS AND METHODS

CONTINUING DATA

This application claims benefit of 61/084,095 file Jul. 28, 2008.

FIELD OF THE INVENTION

The present invention includes compounds that are glucocorticoid receptor modulators. The present invention also includes compositions and methods of using compounds and compositions.

BACKGROUND OF THE INVENTION

Glucocorticoid receptor modulators are glucocorticoid receptor ligands that are used to treat a variety of conditions because of their powerful anti-inflammatory, antiproliferative and immunomodulatory activity. J. Miner, et al., Expert Opin. Investig. Drugs (2005) 14(12):1527-1545.

Examples of glucocorticoid receptor modulators include dexamethasone, prednisone, prednisolone, RU-486, and as described in WO 2000/66522 and WO 2004/005229.

Treatment with glucocorticoid receptor modulators is often associated with side effects, such as bone loss and osteoporosis.

Identifying a glucocorticoid receptor modulator that is efficacious, potent, and has mitigated side-effects fulfills a medical need.

SUMMARY OF THE INVENTION

This invention relates to a compound of Formula I:

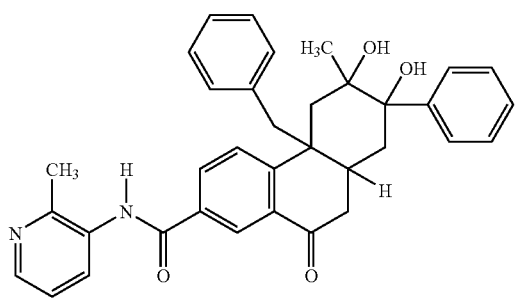

(I)

or salt thereof. This includes the compound 4b-benzyl-6,7-dihydroxy-6-methyl-N-(2-methylpyridin-3-yl)-10-oxo-7-phenyl-4b,5,6,7,8,8a,9,10-octahydrophenanthrene-2-carboxamide or a pharmaceutically acceptable salt thereof.

The invention also relates to compositions comprising a therapeutically effective amount of a compound of Formula I and a pharmaceutically acceptable carrier. Also provided is a method of contacting a glucocorticoid receptor with a compound of Formula I. Further provided are methods of treating a condition in a subject mediated by glucocorticoid receptor activity by administering to the subject a compound of Formula I.

DETAILED DESCRIPTION

This detailed description herein is intended only to acquaint others skilled in the art with the inventions, the principles, and the practical applications so that others skilled in the art may adapt and apply the inventions in their numerous forms, as they may be best suited to the requirements of a particular use. These inventions, therefore, are not limited to the embodiments described in this specification, and may be modified.

A. DEFINITIONS

For the following defined terms, these definitions shall be applied, unless a different definition is given in the claims or elsewhere in this specification.

The term "carrier" describes an ingredient in a pharmaceutical composition or formulation other than an active pharmaceutical compound. Carriers may be a pharmaceutically acceptable material or vehicle or combinations of one or more materials and/or vehicles. Examples include liquid or solid fillers, diluents, excipients, solvents, co-solvents, buffering agents, preservatives, antioxidants, wetting agents, disintegrants, binding agents, suspending agents, surfactants, wetting agents, bulking agents, polymers, glidants, colorants, flavoring agents, sweeteners, lubricants, humectants, and tableting or encapsulating materials.

The phrase "contacting a glucocorticoid receptor" means in vivo, ex vivo, or in vitro contact is made with a glucocorticoid receptor and includes administration of a compound or salt of the present invention to a subject having a glucocorticoid receptor, as well as, for example, introducing a compound or salt of the invention into a sample containing a cellular, unpurified, or purified preparation containing the glucocorticoid receptor. For example, contacting includes interactions between the compound and the receptor, such as binding.

The phrase "inflammation related condition" includes arthritis, fibromyalgia, ankylosing spondylitis, psoriasis, systemic lupus erythematosus, gout, undifferentiated spondyloarthropy, juvenile-onset spondyloarthritis, Crohn's disease, ulcerative colitis, irritable bowel syndrome, inflammatory bowel disease and pain associated with the aforementioned conditions. Specific examples of arthritis include rheumatoid arthritis, osteoarthritis, reactive arthritis, infectious arthritis, psoriatic arthritis, polyarthritis, juvenile arthritis, juvenile rheumatoid arthritis, juvenile reactive arthritis, and juvenile psoriatic arthritis.

The term "modulation" or "modulators" includes antagonist, agonist, partial antagonists, partial agonists, or mixtures or ratios thereof.

The term "subject" refers to any animal, including mammals, such as mice, rats, other rodents, rabbits, dogs, cats, pigs, cattle, sheep, horses, primates, or humans.

The term "treating" (and corresponding terms "treat" and "treatment") includes palliative, restorative, and preventative ("prophylactic") treating of a subject. The term "palliative treating" refers to treatment that eases or reduces the effect or intensity of a condition in a subject without curing the condition. The term "preventative treating" (and the corresponding term "prophylactic treating") refers to treatment that prevents the occurrence of a condition in a subject. The term "restorative treating" ("curative") refers to treatment that halts the progression of, reduces the pathologic manifestations of, or entirely eliminates a condition in a subject. Treating can be done with a therapeutically effective amount of compound, salt or composition that elicits the biological or medicinal response of a tissue, system or subject that is being sought by an individual such as a patient, researcher, doctor, veterinarian, or clinician.

The terms "pharmaceutically effective" or "therapeutically effective" refer to an amount of a compound herein, or salt thereof, that is sufficient to provide an effective treatment, as discussed above. It is understood that what comprises a pharmaceutically or therapeutically effective amount may be a lesser amount of the compound or salt when it is administered in combination with another agent than when utilized alone.

B. COMPOUNDS

The present invention provides tricyclic compounds of Formula I. These compounds are useful as glucocorticoid receptor modulators.

The present invention also comprises a compound of Formula II:

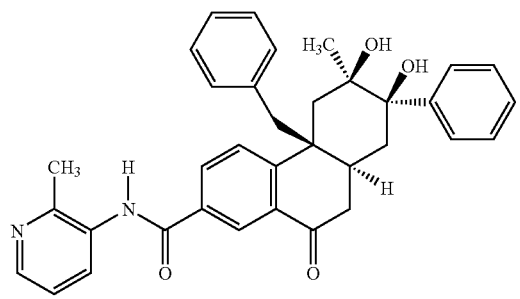

(II)

or salt thereof.

The present invention includes the compound 4b-benzyl-6,7-dihydroxy-6-methyl-N-(2methylpyridin-3-yl)-10-oxo-7-phenyl-4b,5,6,7,8,8a,9,10-octahydrophenanthrene-2-carboxamide or a pharmaceutically acceptable salt thereof. Also included is the compound (4bR,6R,7R,8aS)-4b-benzyl-6,7-dihydroxy-6-methyl-N-(2-methylpyridin-3-yl)-10-oxo-7-phenyl-4b,5,6,7,8,8a,9,10-octahydrophenanthrene-2-carboxamide or pharmaceutically acceptable salt thereof.

Pharmaceutically acceptable salts of compounds of the present invention include the acid addition and base salts (including disalts) thereof. In one embodiment, the present invention includes a hydrochloride salt of the compound of Formula I. In another embodiment, the present invention includes a calcium salt of the compound of Formula I. In another embodiment, the present invention includes a sodium salt of the compound of Formula I.

Pharmaceutically acceptable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Pharmaceutically acceptable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A salt may be readily prepared by mixing together solutions of compounds of the present invention and the desired acid or base, as appropriate. The salt may precipitate from solution and be collected by filtration or may be recovered by evaporation of the solvent. The degree of ionization in the salt may vary from completely ionized to almost non-ionized.

The compounds of the present invention may be administered as prodrugs. Thus, certain derivatives which may have little or no pharmacological activity themselves can, when administered into or onto the body, be converted into compounds of the present invention having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in the compounds of the present invention with certain moieties known to those skilled in the art as 'pro-moieties' as described, for example, in "Design of Prodrugs" by H Bundgaard (Elsevier, 1985).

Some examples of such prodrugs include:

(i) where the compound contains an alcohol functionality (—OH), an ether thereof, for example, replacement of the hydrogen with $(C_1-C_6)$alkanoyloxymethyl; and (ii) where the compound contains a secondary amino functionality, an amide thereof, for example, replacement of hydrogen with $(C_1-C_{10})$alkanoyl.

Phosphate forms of the compounds herein may be prepared by methods known in the art, such as those disclosed in WO 2008/070149, WO 2008/064274 and WO 2006/078846. The compound (4a-benzyl-2,3-dihydroxy-3-methyl-N-(2-methylpyridin-3-yl)-9-oxo-2-phenyl-1,2,3,4,4a,9,10,10a-octahydrophenanthrene-7-carboxamido)methyl dihydrogen phosphate and stereoisomer ((2R,3R,4aR10aS)-4a-benzyl-2,3-hydroxy-3-methyl-N-(2-methylpyridin-3-yl)-9-oxo-2-phenyl-1,2,3,4,4a,9,10,10a-octahydrophenanthrene-7-carboxamido)methyl dihydrogen phosphate may be prepared by the scheme below:

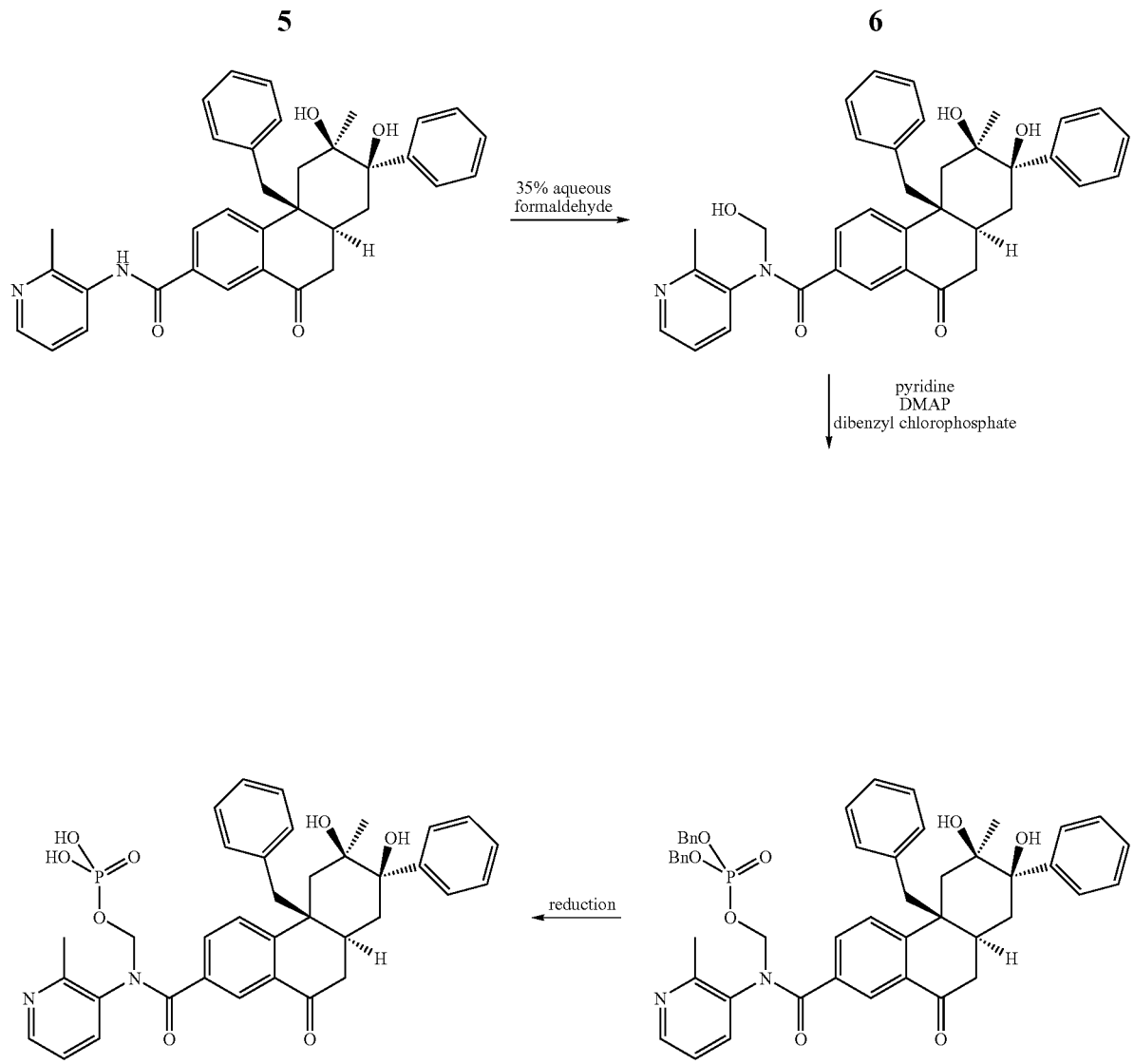

Finally, certain compounds of the present invention may themselves act as prodrugs of other compounds of the present invention. For example, certain compounds of Formula I or II could be viewed as a prodrug of other compounds encompassed by Formula I or II.

All isomers, such as stereoisomers, geometric (cis/trans or Z/E) isomers and tautomeric forms of the compounds or salts are included in the scope of the present invention, including compounds or salts having more than one type of isomerism, and mixtures of one or more thereof. For example, the following depicts a compound of Formula II and a tautomer.

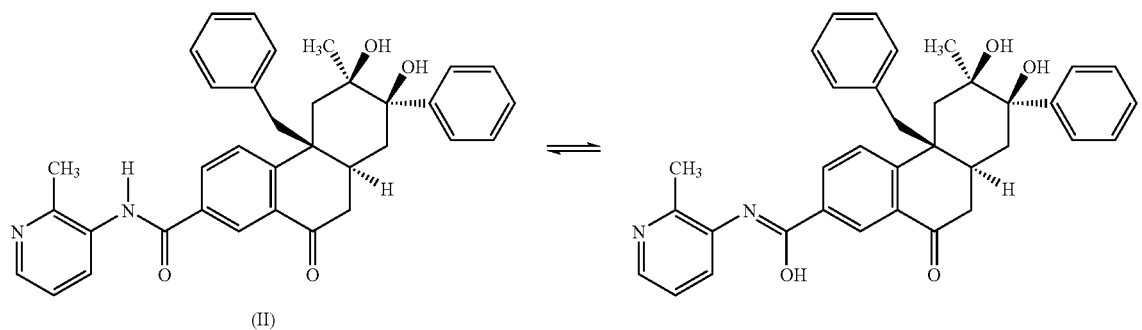

Also included are acid addition or base salts wherein the counterion is optically active, for example, D-lactate or L-lysine, or racemic, for example, DL-tartrate or DL-arginine.

Isomers may be separated by conventional techniques well known to those skilled in the art.

The present invention includes isotopically-labeled compounds of the invention wherein one or more atoms are replaced by atoms having the same atomic number, but an atomic mass or mass number different from the atomic mass or mass number usually found in nature.

Isotopically-labeled compounds of the invention can generally be prepared by conventional techniques known to those skilled in the art or by processes analogous to those described in the accompanying Examples and Preparations using an appropriate isotopically-labeled reagent in place of the non-labeled reagent previously employed.

For the treatment of the conditions referred to below, the compounds of the present invention can be administered. Salts of the compounds of the present invention could also be used.

C. COMPOSITIONS

Compounds or salts of the present invention may be part of a composition. Compositions can also include one or more compounds or salts of the present invention. The composition can also include an enantiomeric excess of one or more compounds of the present invention. Other pharmacologically active substances and carriers can be included in the composition.

One embodiment is a composition comprising a compound of Formula I or a salt thereof. Another embodiment is a composition comprising a compound of Formula I or a salt thereof and a carrier.

For example, the carrier can be an excipient. The choice of excipient will to a large extent depend on factors such as the particular mode of administration, the effect of the excipient on solubility and stability, and the nature of the dosage form.

The composition can be a solid, a liquid, or both, and may be formulated with the compound as a unit-dose composition, for example, a tablet, which can contain from 0.05% to 95% by weight of the active compounds. Compounds or salts of the present invention may be coupled with suitable polymers or other drug carriers.

D. METHODS

The present invention includes a method of contacting a glucocorticoid receptor with a compound or salt of the present invention.

The present invention also includes a method of treating a condition mediated by glucocorticoid receptor activity in a subject comprising administering to the subject a compound or salt of the present invention.

A condition mediated by glucocorticoid receptor activity includes:

a) endocrine disorders, such as primary or secondary adrenocortical insufficiency, congenital adrenal hyperplasia, nonsuppurative thyroiditis, and hypercalcemia associated with cancer;

b) rheumatic disorders, such as psoriatic arthritis, rheumatoid arthritis, including juvenile rheumatoid arthritis, ankylosing spondylitis, acute and subacute bursitis, acute nonspecific tenosynovitis, acute gouty arthritis, post-traumatic osteoarthritis, synovitis of osteoarthritis, and epicondylitis;

c) collagen diseases, such as systemic lupus erythematosus, and acute rheumatic carditis;

d) dermatologic conditions, such as pemphigus, bullous dermatitis herpetiformis, severe erythema multiforme (Stevens-Johnson syndrome), exfoliative dermatitis, mycosis fungoides, psoriasis, and seborrheic dermatitis;

e) allergic states, such as seasonal or perennial allergies, allergic rhinitis, bronchial asthma, contact dermatitis, atopic dermatitis, serum sickness, and drug hypersensitivity reactions;

f) ophthalmic diseases and conditions, such as allergic corneal marginal ulcers, herpes zoster ophthalmicus, anterior segment inflammation, diffuse posterior uveitis and choroiditis, chronic uveitis, sympathetic ophthalmia, allergic conjunctivitis, keratitis, chorioretinitis, optic neuritis, iritis and iridocyclitis;

g) respiratory diseases, such as symptomatic sarcoidosis, Loeffler's syndrome, berylliosis, fulminating or disseminated pulmonary tuberculosis, and aspiration pneumonitis;

h) hematologic disorders, such as idiopathic thrombocytopenic purpura, secondary thrombocytopenia, acquired (autoimmune) hemolytic anemia, erythroblastopenia (Red Blood Cell anemia), and congenital (erythroid) hypoplastic anemia;

i) neoplastic diseases, such as leukemia and lymphoma;

j) edematous states, such as inducing diuresis or emission of proteinuria in the nephrotic syndrome, without uremia, of the idiopathic type or that due to lupus erythematosus;

k) gastrointestinal diseases, such as ulcerative colitis, regional enteritis, inflammatory bowel disease, Crohn's disease, gastritis, irritable bowel syndrome;

l) miscellaneous conditions, such as tuberculous meningitis and trichinosis; and m) neurological conditions, such as Alzheimer's disease, Parkinson's disease, Huntington's disease, amyotrophic lateral sclerosis, spinal cord injury, psychotic major depression, and peripheral neuropathy.

A condition mediated by glucocorticoid receptor activity also includes transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitelego (depigmentation of the skin), alopecia areata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and atherosclerosis.

A condition mediated by glucocorticoid receptor activity also includes:

a) asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis;

b) chronic or acute bronchoconstriction, chronic bronchitis, small airways obstruction, and emphysema;

c) obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension;

d) bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, acute lung injury; and e) bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

Another embodiment includes a use of a compound or salt of the present invention for use in treating obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, or asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

The present invention includes a method of treating an inflammation-related condition in a subject comprising administering to the subject a compound or salt of the present invention.

The present invention includes a method of treating conditions such as asthma, dermatitis, inflammatory bowel disease, Alzheimer's disease, psychotic major depression, neuropathy, transplant rejection, multiple sclerosis, chronic uveitis, or chronic obstructive pulmonary disease in a subject comprising administering to the subject a compound or salt of the present invention.

The present invention includes a method of treating rheumatoid arthritis in a subject comprising administering to the subject a compound or salt of the present invention.

Rheumatoid arthritis is considered a chronic autoimmune and inflammatory disease producing inflamed joints, which eventually swell, become painful, and experience degradation of cartilage, bone, and ligaments of the joint. A result of rheumatoid arthritis is deformity, instability, and stiffness of the joint and scarring within the joint. The joints deteriorate at a highly variable rate. Many factors, including genetic predisposition, may influence the pattern of the disease. People with rheumatoid arthritis may have a mild course, occasional flare-ups with long periods of remission without disease, or a steadily progressive disease, which may be slow or rapid. Rheumatoid arthritis may start suddenly, with many joints becoming inflamed at the same time. More often, it starts subtly, gradually affecting different joints. Usually, the inflammation is symmetric, with joints on both sides of the body affected. Typically, the small joints in the fingers, toes, hands, feet, wrists, elbows, and ankles become inflamed first, followed by the knees and hips.

Pain associated with rheumatoid arthritis is typically somatic nociceptive joint pain. Swollen wrists can pinch a nerve and result in numbness or tingling due to carpal tunnel syndrome. Cysts may develop behind affected knees, can rupture, causing pain and swelling in the lower legs.

The present invention includes a method of treating dermatitis in a subject comprising administering to the subject a compound or salt of the present invention.

The present invention includes a method of treating chronic obstructive pulmonary disease in a subject comprising administering to the subject a compound or salt of the present invention.

The present invention includes a method of treating asthma in a subject comprising administering to the subject a compound or salt of the present invention.

The present invention includes a method of treating Alzheimer's disease in a subject comprising administering to the subject a compound or salt of the present invention.

The present invention includes a method of mitigating side effects associated with glucocorticoid receptor modulation, comprising administering a compound of Formula I to a subject.

The present invention includes a method of mitigating side effects associated with prednisolone treatment, comprising administering a compound of Formula I to a subject.

The present invention further comprises methods of treating the aforementioned conditions, diseases, and disorders in a subject or a subject susceptible to having such a condition, by administering to the subject one or more compounds or salts of the present invention.

In one embodiment, the aforementioned treatment is preventative treatment.

In another embodiment, the aforementioned treatment is palliative treatment.

In another embodiment, the aforementioned treatment is restorative treatment.

E. DOSAGE AND ADMINISTRATION

To select the most appropriate dosage form and route of administration for treatment of the proposed indication, the compounds or salts of the invention can be assessed for their biopharmaceutical properties, such as solubility and solution stability (across pH), and permeability.

Doses for compounds or salts of the invention range from 0.1 mg to 100 mg for oral administration and doses range from 2 mg or less for inhaled administration. The dose may be administered in single dose or two or more divided doses and may fall outside of the typical range given herein.

The dosages are based on an average human subject having a weight of about 60 kg to 70 kg. Dosing and dosing regimen depend upon subject and a variety of conditions that may affect dosing (age, sex, body weight, etc.). A physician or other medical professional will readily be able to determine doses for subjects whose weight falls outside this range, such as infants and the elderly.

Oral Administration

The compounds of the invention and salts thereof may be administered orally. Oral administration may involve swallowing, so that the compound or salt enters the gastrointestinal tract, and/or buccal, lingual, or sublingual administration by which the compound or salt enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches. Further, the compound or salts of the invention can be administered as a spray dried dispersion.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention and salts thereof may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001).

Dose ranges for oral administration also include from 0.1 mg to 80 mg, 15 mg to 80 mg, 0.1 mg to 25 mg.

Parenteral Administration

The compounds or salts of the invention may also be administered directly into the blood stream, into muscle, or into an internal organ. Example 2 could be administered into the blood stream. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of the present invention and salts thereof used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

Topical Administration

The compounds or salts of the invention may also be administered topically, (intra)dermally, or transdermally to the skin or mucosa. Example 1 could be administered to the skin. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds or salts of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid. Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics may comprise a compound of the present invention, propylene glycol, sterile water, ethanol and sodium chloride. Alternative solvents which may be used instead of propylene glycol include glycerol and polyethylene glycol.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" which may be administered in a single dose or, more usually, as divided doses throughout the day.

Dose ranges for inhaled administration range from 2 mg to less or 1 mg to less.

Combination

The compounds or salts of the invention may be administered in combination with one or more other therapeutic agents, such as a drug. The compound of the present invention or salt thereof may be administered at the same time or different time as one or more other therapeutic agents.

For example, "in combination" includes: simultaneous administration of a combination of compound or salt of the invention and a therapeutic agent to a subject, when such components are formulated together into a single dosage form which releases said components at substantially the same time to said subject; substantially simultaneous administration of a combination of compound or salt of the invention and a therapeutic agent to a subject in need of treatment, when such components are formulated apart from each other into separate dosage forms which are taken at substantially the same time by said subject, whereupon said components are released at substantially the same time to said subject; sequential administration of a combination of compound or salt of the invention and a therapeutic agent to a subject, when such components are formulated apart from each other into separate dosage forms which are taken at consecutive times by said subject with a significant time interval between each administration, whereupon said components are released at substantially different times to said subject; and sequential administration of such combination of compound or salt of the invention and a therapeutic agent to a subject, when such components are formulated together into a single dosage form which releases said components in a controlled manner whereupon they are concurrently, consecutively, and/or overlappingly administered at the same and/or different times by said subject, where each part may be administered by either the same or different route.

For example, the compounds or salts of the present invention may be used in combination, partially or completely, in addition to other anti-inflammatory agents. Examples of pharmaceutical agents that may be used in combination with the compounds and salts described herein include TNF-α inhibitors, COX-2 inhibitors, 5-lipoxygenase inhibitors, receptor antagoinists for leukotrienes, PDE4 inhibitors, antihistaminic $H_1$ inhibitors, gastroprotective $H_2$ receptor antagoinists, insulin-like growth factor type (IGF-1) mimetics, inhibitors of matrix metalloproteases, non-steroidal anti-inflammatory agents, p38 inhibitors, P2X7 inhibitors, α2Δ inhibitors, antiviral agents, and other agents described on pages 32-38 of WO 2004/005229.

F. USE IN THE PREPARATION OF A COMPOSITION OR MEDICAMENT

In one embodiment, the present invention comprises methods for the preparation of a composition or medicament comprising the compounds or salts of the present invention for use in treating condition mediated by glucocorticoid receptor activity.

In another embodiment, the invention comprises the use of one or more compounds or salts of the present invention in the preparation of a composition or a medicament for inflammation, inflammation related condition, rheumatoid arthritis, dermatitis, Alzheimer's disease.

The present invention also includes the use of one or more compounds or salts of the present invention for preparation of a composition or a medicament for treating one or more conditions detailed in the Methods section.

G. SCHEMES

The compounds of the present invention may be prepared using the methods illustrated in the general synthetic schemes and experimental procedures detailed below. The reactions of the synthetic methods herein are carried out in suitable solvents which may be readily selected by one skilled in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

Preparation of Compounds of the Invention can Involve the Protection and Deprotection of Various chemical groups. The need for protection and deprotection, and the selection of appropriate protecting groups can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The starting materials used herein are either commercially available or may be prepared by routine synthetic methods.

The general synthetic schemes are presented for purposes of illustration and are not intended to be limiting.

SCHEME A

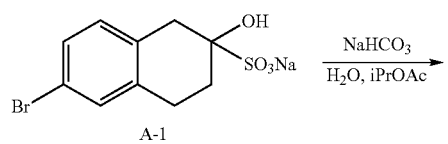

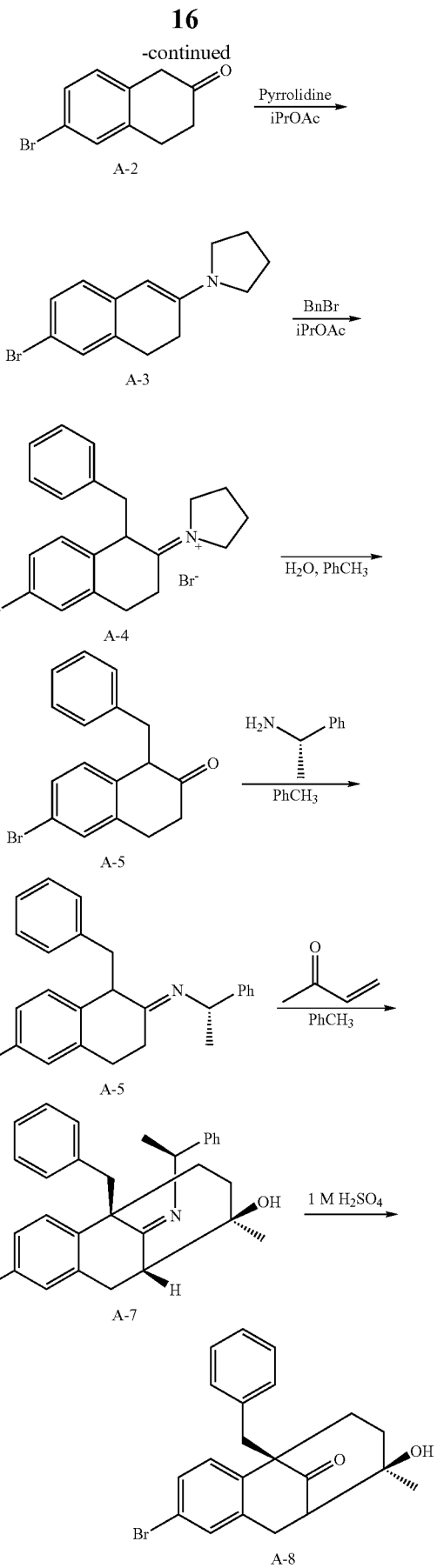

The 1(R)-Benzyl-5-bromo-9(S)-hydro-10(R)-hydroxy-10(R)-methyl-tricyclo[7.3.1.0$^{2,7}$]-trideca-2,4,6-trien-13-one of Formula A-8 was prepared using the protocol described in Scheme A, which is generally disclosed in WO 00/66522. Ph depicts Phenyl. Bn depicts Benzyl. Compound A-1 can be purchased (for example, (Sanmar, Vuf, Kingchem). Compound A-2,6-bromo-3,4-dihydro-2(1H)-naphthalenone (Chem. Abstr. Reg. No. 4133-35-1), can be prepared as described in Org. Syn. 1971, 51, 109-112. Compound A-3,1-(6-bromo-1,2,3,4-tetrahydro-2-naphthalenyl)-pyrrolidine (Chem. Abst. Reg. No. 863925-40-0) as described in WO 2007/105053 (McHardy et al.). Compound A-4,1-[6-bromo-3,4-dihydro-1-(phenylmethyl)-2-(1H)-naphthalenylidene]-pyrrolidinium bromide (Chem. Abstr. Reg. No. 418772-22-2) is also described in US 2002/0107235 (Liu et al.) and U.S. Pat. No. 6,852,719 (Liu et al.).

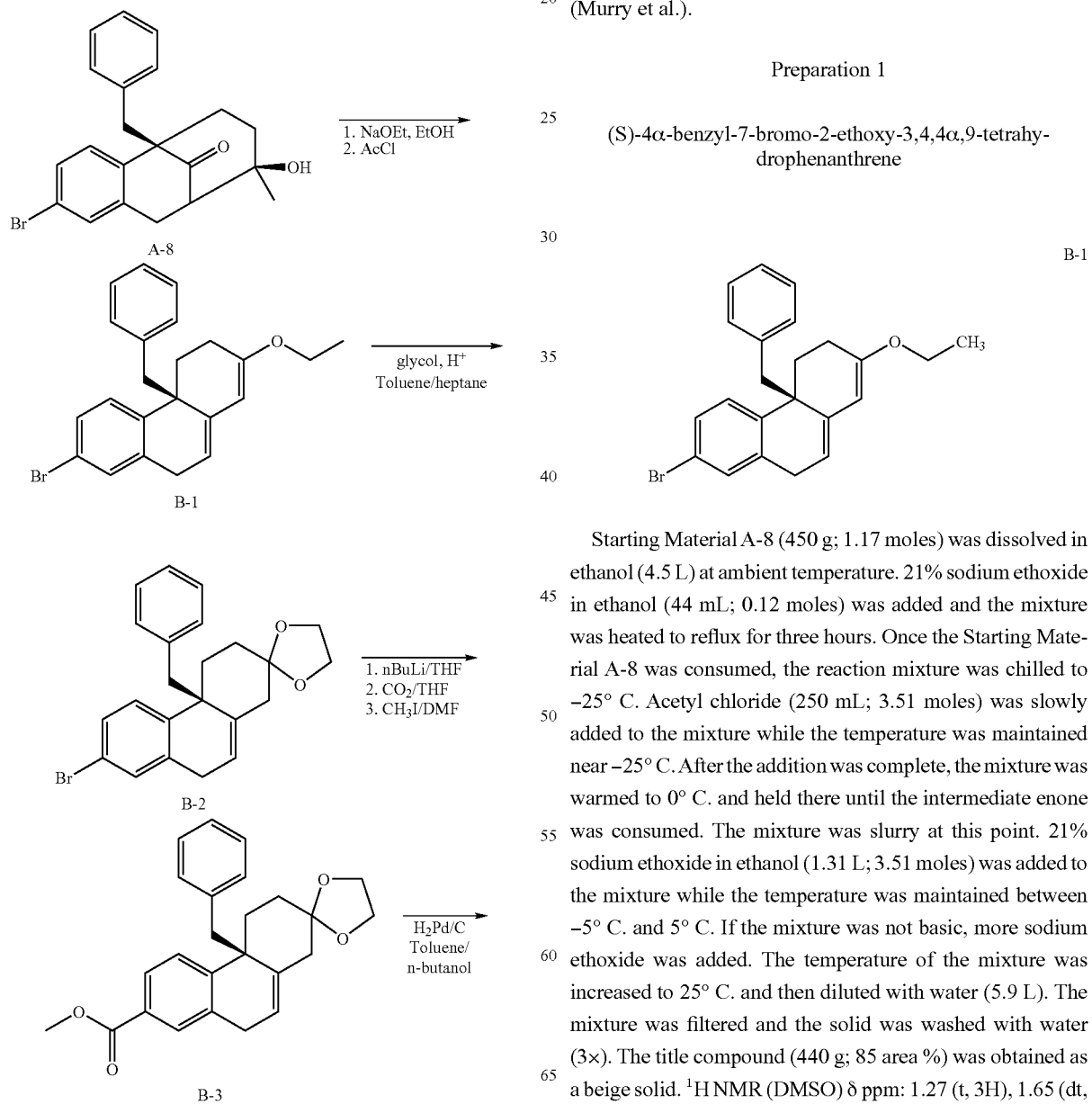

The compound B-1,7-bromo-2-ethoxy-3,4,4a,9-tetrahydro-4a-(phenylmethyl)-(4aS)-phenanthrene, may be prepared as described in European Patent Applications EP 1201649 and EP 1201660 (both to Liu et al.) and EP 1201665 (Murry et al.).

Preparation 1

(S)-4α-benzyl-7-bromo-2-ethoxy-3,4,4α,9-tetrahydrophenanthrene

Starting Material A-8 (450 g; 1.17 moles) was dissolved in ethanol (4.5 L) at ambient temperature. 21% sodium ethoxide in ethanol (44 mL; 0.12 moles) was added and the mixture was heated to reflux for three hours. Once the Starting Material A-8 was consumed, the reaction mixture was chilled to −25° C. Acetyl chloride (250 mL; 3.51 moles) was slowly added to the mixture while the temperature was maintained near −25° C. After the addition was complete, the mixture was warmed to 0° C. and held there until the intermediate enone was consumed. The mixture was slurry at this point. 21% sodium ethoxide in ethanol (1.31 L; 3.51 moles) was added to the mixture while the temperature was maintained between −5° C. and 5° C. If the mixture was not basic, more sodium ethoxide was added. The temperature of the mixture was increased to 25° C. and then diluted with water (5.9 L). The mixture was filtered and the solid was washed with water (3×). The title compound (440 g; 85 area %) was obtained as a beige solid. $^1$H NMR (DMSO) δ ppm: 1.27 (t, 3H), 1.65 (dt, 1H), 2.06 (d, 1H), 2.21 (dd, 1H), 2.49 (m, 1H), 2.65 (m, 2H), 2.89 (m, 2H), 3.85 (q, 2H), 5.45 (m, 2H), 6.44 (d, 2H), 6.98 (t, 2H), 7.06 (m, 2H), 7.25 (d, 1H), 7.33 (dd, 1H).

Preparation 2

(S)-4α-benzyl-7-bromo-2,2-(1,2-ethylenedioxy)-1,2,3,4,4α,9-hexahydrophenanthrene

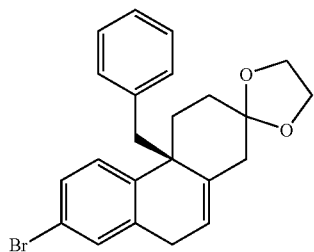

B-2

The (S)-4α-benzyl-7-bromo-2-ethoxy-3,4,4α,9-tetrahydrophenanthrene (1270 g; 3.2 moles; 85 area %, which may be prepared as described in Preparation 1) was dissolved in toluene (6.45 L). The ethylene glycol (898 mL; 16.1 moles) and p-toluenesulfonic acid (6.1 g; 0.03 moles) were added and the reaction heated to reflux. Solvent (1 L) was distilled from the mixture and replaced with fresh toluene (1 L). This distillation process was repeated twice more. More p-toluenesulfonic acid (6.1 g) was added each time fresh toluene was added. During the reaction, two intermediates (detected by LC) were formed as the substrate was converted into product. The end point of the reaction was an equilibrium point between the two intermediates and the product. Once the endpoint was reached, the mixture was cooled to ambient temperature. The mixture was washed with 0.5 M NaOH (2 L). The phases separated quickly and both were dark with a small rag layer. The mixture was washed with water (2 L). The phases separated very slowly. The mixture was dried by azeotropic distillation. Methanol (4 L) was added to the mixture and solvent (4 L) was distilled from the mixture. The methanol addition and solvent distillation were repeated twice more. Methanol was added to the mixture and precipitation occurred a few minutes later. More methanol (4 L) was added to the mixture and then brought to reflux. After 30 minutes, the mixture was cooled to 0° C. The mixture was filtered and the solid was washed with chilled methanol (2×2 L). The solid was dried in a vacuum oven at 65° C. The title compound (882 g; 98 area %) was obtained as a beige solid. $^1$H NMR (DMSO) δ ppm: 1.71 (m, 2H), 2.06 (m, 2H), 2.31 (dd, 1H), 2.39 (m, 1H), 2.68 (d, 1H), 2.77 (m, 1H), 2.86 (dd, 1H), 3.36 (d, 1H), 3.86 (m, 4H), 5.45 (m, 1H), 6.50 (m, 2H), 7.00 (m, 4H), 7.37 (dd, 1H), 7.44 (d, 1H).

Preparation 3

(S)-methyl 4β-benzyl-7,7-(1,2-ethylenedioxy)-4β,5,6,7,8,10-hexahydrophenanthrene-2-carboxylate

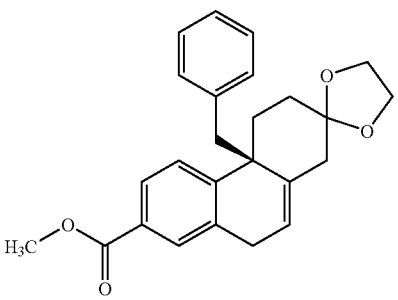

B-3

The (S)-4□-benzyl-7-bromo-2,2-(1,2-ethylenedioxy)-1,2,3,4,4□,9-hexahydrophenanthrene (719 g; 1.75 moles, which may be prepared as described in Preparation 2) was dissolved in tetrahydrofuran (7.19 L) and chilled to −70° C. The 1.6 M n-butyl lithium in hexane (2270 mL; 2.27 moles) was added at a rate such that the temperature was maintained below −60° C. The mixture held an additional 15 minutes after the addition. Carbon dioxide (108 g; 2.45 moles) was added while the temperature was maintained below −60° C. The mixture held an additional 15 minutes after the addition. The mixture was warmed to ambient temperature. Solvent (7 L) was distilled from the mixture at atmospheric pressure. DMF (7 L) was added to the mixture. The mixture was cooled to ambient temperature. Methyl iodide (152 mL; 2.45 moles) was added and the mixture was held until the reaction was completed (~1 hour). The mixture was heated to 70° C. and solvent was distilled by gradually reducing the pressure to 70 mmHg. Once distillation had ceased, the mixture was cooled to room temperature. Water (6.5 L) was slowly added to the mixture to precipitate the product. The mixture was filtered and the solid washed with water (3×). The solid was dried on the filter. The crude product (736 g; 74 area %) was obtained as a beige solid. The product was purified by chromatography. 463 g of product was recovered from the chromatography. This material was separated from n-heptane (6130 mL). 394 g of the title compound was recovered. Another 70 g of title compound was recovered from the mother liquor by chromatography. $^1$H NMR (DMSO) δ ppm: 1.74 (m, 2H), 2.10 (m, 2H), 2.33 (dd, 1H), 2.45 (m, 1H), 2.72 (d, 1H), 2.79 (m, 1H), 2.94 (dd, 1H), 3.40 (d, 1H), 3.87 (m, 7H), 5.49 (m, 1H), 6.47 (m, 2H), 6.93 (m, 2H), 7.01 (m, 1H), 7.42 (d, 1H), 7.64 (d, 1H), 7.79 (dd, 1H).

Preparation 4

(4βS,8αR)-methyl 4β-benzyl-7,7-(1,2-ethylenedioxy)-4β,5,6,7,8,8α,9,10-octahydrophenanthrene-2-carboxylate

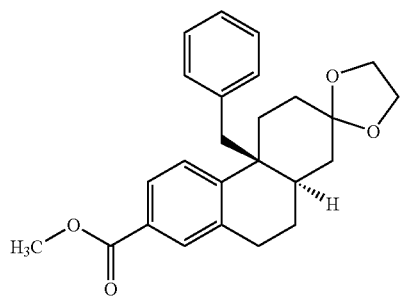

B-4

The (S)-methyl 4β-benzyl-7,7-(1,2-ethylenedioxy)-4β,5,6,7,8,10hexahydrophenanthrene-2-carboxylate (201 g; 0.515 moles, which may be prepared as described in Preparation 3) and 50 ml of ethylene glycol was dissolved in toluene (2.0 L) in an autoclave. To this was added 10 grams of a 5% Pd/C (dry catalyst). The autoclave was then sealed and purged with nitrogen (three cycles) followed by hydrogen (three cycles). The reaction was run for 18 hours with a pressure of 80 psig and temperature of 50° C. HPLC analysis for completion and selectivity (typical selectivity's are: 95 to 5, Trans to C is). The suspension was filtered through Celite® to remove the catalyst and the toluene solution is concentrated at 50° C., under vacuum, to approximately 200 ml. While still at 50° C., 1 L of 1-butanol was added and the solution heated to 60° C., until clear. Upon cooling, the resulting solid title compound was isolated by vacuum filtration (196 grams; 97%; Trans to C is 95.75 to 4.24). $^1$H NMR (300 MHz, CDCl$_3$) δ ppm: 7.79 (bs, 1H, Ar—H), 7.47 (d, J=9 Hz, 1H, Ar—H), 7.13-7.05 (cm, 3H, Ar—H), 6.56-6.53 (cm, 2H, Ar—H), 6.43 (d, J=9 Hz, 1H, Ar—H), 4.04-3.93 (cm, 4H, 2-CH$_2$), 3.89 (s, 3H, CH$_3$), 3.08-3.03 (cm, 3H, CH$_2$, CH—H), 2.63 (d, J=15 Hz, CH—H), 2.22-1.72 (cm, 8H, 4-CH$_2$), 1.57 (cm, 1H, CH—H). $^{13}$CNMR (CDCl$_3$, δ): 167.7, 149.2, 137.7, 136.4, 131.1, 130.5, 127.8, 127.7, 127.4, 126.3, 125.5, 108.9, 64.6, 64.5, 52.1, 40.5, 39.8, 38.3, 35.8, 31.6, 30.3, 27.9, 24.6.

SCHEME C

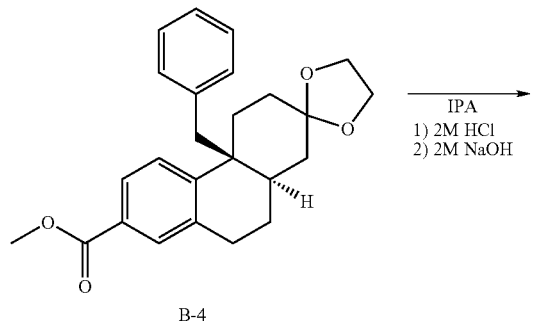

B-4

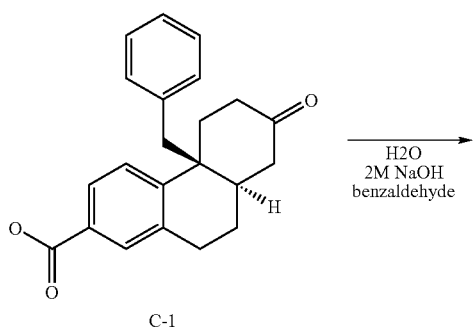

C-1

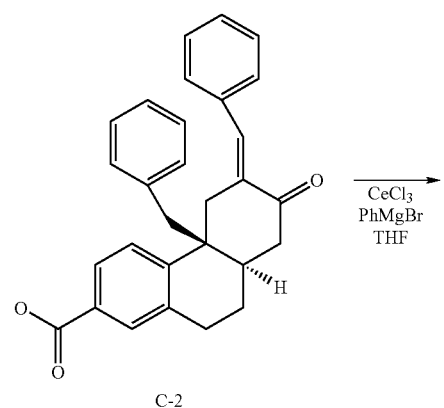

C-2

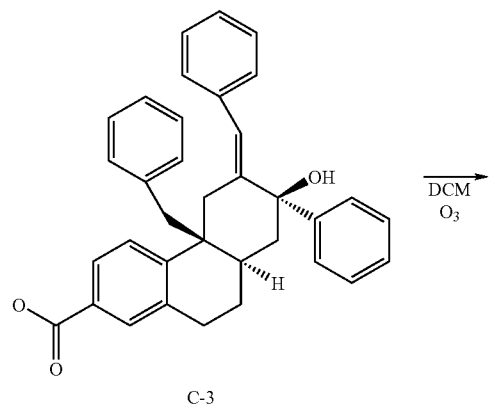

C-3

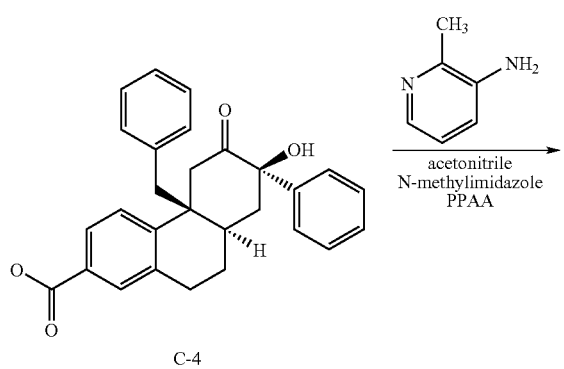

C-4

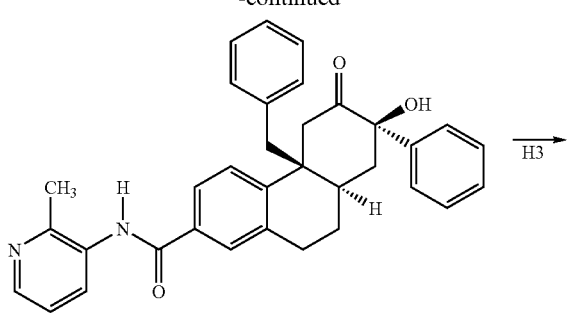

C-5

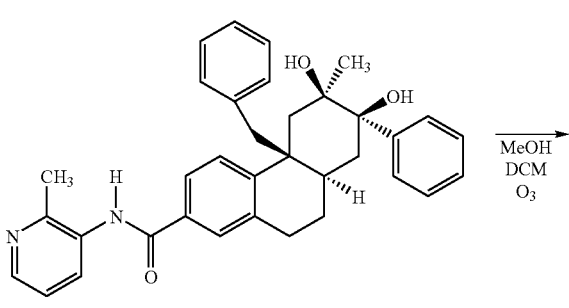

C-6

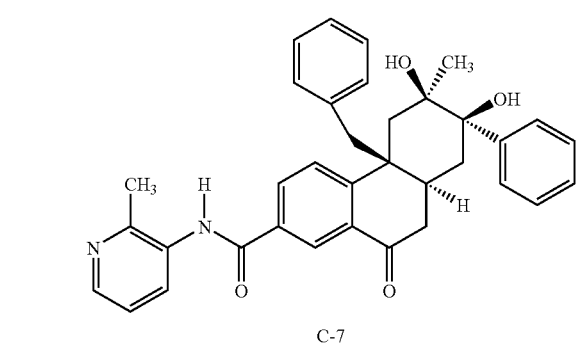

C-7

Preparation 5

(4bS,8aR)-4b-benzyl-7-oxo-4b,5,6,7,8,8a,9,10-octahydrophenanthrene-2-carboxylic acid

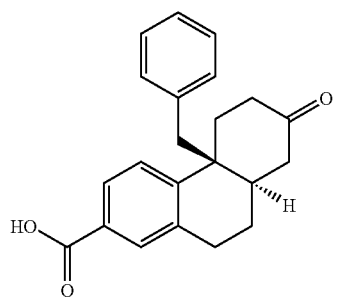

(4βS,8αR)-methyl 4β-benzyl-7,7-(1,2-ethylenedioxy)-4β,5,6,7,8,8α,9,10-octahydrophenanthrene-2-carboxylate (10 g, 25.5 mmol), IPA (75 mL), and aqueous 2 M HCl (25 mL, 51.0 mmol) were mixed together and heated to reflux. The mixture became homogeneous during the heat-up. The mixture was held at reflux until the ketal was hydrolyzed (about 30-45 min). The reaction stopped with about 3% of the ketal remaining. 2.5 M NaOH (40 mL, 101.9 mmol) was added to the mixture and heating was continued. The mixture was held at reflux until the ester was hydrolyzed (about 30 min). Aqueous 2 M HCl (40 mL) was added and the mixture was cooled to 40° C. Two liquid phases formed as the acid was added. Seed crystals were added to initiate crystallization. More aqueous 2 M HCl (40 mL) was added 30 minutes after crystallization had started. The mixture was cooled to 20° C. and held for 60 minutes. The mixture was filtered and the solid was washed with water. The solid was dried in a vacuum oven at 70° C. A pale yellow solid (7.86 g, 92% yield) was obtained. $^1$H NMR (DMSO): δ 1.50 (m, 1H), 1.65 (m, 1H), 1.90 (m, 1H), 2.05 (m, 1H), 2.20 (d, 1H), 2.30 (d, 1H), 2.40 (dd, 1H), 2.65 (d, 1H), 2.80 (d, 1H), 3.00 (m, 3H), 4.30 (d, 1H), 6.40 (d, 1H), 6.60 (d, 2H), 7.10 (m, 3H), 7.35 (d, 1H), 7.65 (s, 1H), 12.75 (s, 1H).

Preparation 6

(4bR,6E,8aR)-4b-benzyl-6-benzylidene-7-oxo-4b,5,6,7,8,8a,9,10-octahydrophenanthrene-2-carboxylic acid

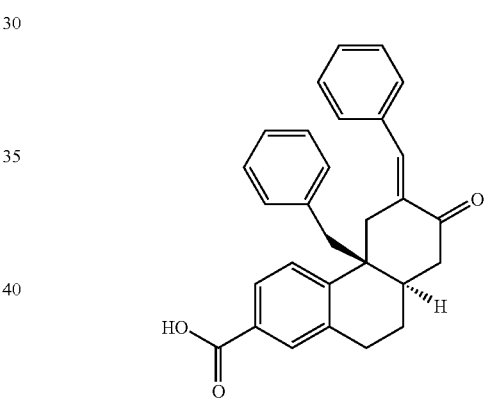

(4bS,8aR)-4b-benzyl-7-oxo-4b,5,6,7,8,8a,9,10-octahydrophenanthrene-2-carboxylic acid (6.5 g, 19.44 mmol) was suspended in water (65 mL). 2.5 M NaOH (11.7 mL, 29.16 mmol) was added followed by benzaldehyde (2.16 mL, 21.38 mmol). Over time (at 50° C. for 4 hours or at 25° C. over night) the mixture became homogeneous. The reaction was considered complete when there was less than 2% of (4bS,8aR)-4b-benzyl-7-oxo-4b,5,6,7,8,8a,9,10-octahydrophenanthrene-2-carboxylic acid (Preparation 5) remaining. The mixture was cooled to 25° C. if it was not already at 25° C. EtOAc (65 mL) was added to the mixture followed by aqueous 2 M HCl (29 mL). Crystallization normally occurred during the acid addition or shortly thereafter. The mixture was stirred for 60 minutes. Heptane (65 mL) was added and the mixture was stirred for an additional 60 minutes. Do not worry about separating out the aqueous phase; filter the entire mixture and wash the solid with water followed by heptane. A pale yellow solid (6.55 g, 80% yield) was obtained. $^1$H NMR (DMSO): δ 1.70 (m, 1H), 1.85 (m, 1H), 2.45 (m, 3H), 2.65 (d, 3H), 2.95 (m, 2H), 3.50 (d, 1H), 6.15 (d, 2H), 6.25 (d, 1H), 6.70 (t, 2H), 6.90 (t, 1H), 7.30 (d, 1H), 7.50 (m, 5H), 7.70 (d, 2H), 12.75 (s, 1H).

Preparation 7

(4bR,6E,7S,8aR)-4b-benzyl-6-benzylidene-7-hydroxy-7-phenyl-4b,5,6,7,8,8a,9,10-octahydrophenanthrene-2-carboxylic acid

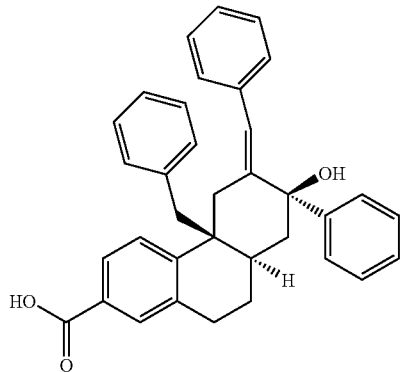

Cerium (III) Chloride (5.00 g, 20.29 mmol) was mixed in tetrahydrofuran (50 mL) at 50° C. for 16 hours. The temperature of the reaction was internally monitored with a JKEM. The resulting white milky solution was cooled to −75 C and stirred vigorously. The cold slurry was charged with phenyl magnesium bromide (1.0 M in THF, 19.1 mmol) dropwise over 15 minutes with the temperature maintained below −70° C. The solution was kept at −73° C. for 15 minutes and a solution of (4bR,6E,8aR)-4b-benzyl-6-benzylidene-7-oxo-4b,5,6,7,8,8a,9,10-octahydrophenanthrene-2-carboxylic acid (3.5 g, 8.311 mmol) in tetrahydrofuran (40 mL) was added dropwise over 20 minutes maintaining the reaction temperature below −70° C. HPLC/MS was obtained and indicated remaining starting material. The reaction was mixed for an additional 3 hours and an HPLC/MS was obtained and starting material remained. An additional 2 mL of benzyl magnesium bromide solution (2.0 mmol) was added over 10 minutes and an HPLC/MS obtained. An additional 1 mL of benzyl magnesium bromide solution (1.0 mmol) was added over 10 minutes and an HPLC/MS obtained. The solution was mixed for 30 minutes at −73° C. and allowed to warm to 10° C. and then cooled to 0° C. The reaction was quenched by the addition of saturated aqueous $KHSO_4$ dropwise maintaining the temperature below 10° C. A total of 50 ml of the saturated solution was added. Solids formed in the solution and were removed by vacuum filtratration. The filter cake was washed with tetrahydrofuran (40 mL) and water (40 mL). Ethyl acetate (100 mL) was added and the layers separated. The organic layer was washed with saturated ammonium chloride (100 mL), dried over sodium sulfate, and solvent removed at reduced pressure. The aqueous layer was checked by HPLC/MS and did not contain any product. The residue was taken up in methanol (15 ml) and water added. The solution became milky and eventually a precipitate formed. Small amounts of methanol and water were added to improve the quality and quantity of precipitate. The solids were collected by vacuum filtration and air dried for about 2 hours. 3.4 grams of the title compound as a light yellow solid was obtained in 81% yield. $^1$H NMR (400 MHz, DMSO-$d_6$) d ppm 12.65 (1H, s), 7.44-7.56 (7H, m), 7.34-7.39 (2H, m), 7.30 (2H, t, J=7.7 Hz), 7.12-7.22 (2H, m), 6.78 (1H, t, J=7.4 Hz), 6.50 (2H, t, J=7.8 Hz), 6.12 (1H, d, J=8.3 Hz), 5.86 (2H, d, J=7.3 Hz), 5.44 (1H, s), 3.61 (1H, d, J=14.2 Hz), 2.96 (1H, dd, J=17.6, 7.9 Hz), 2.80-2.91 (1H, m), 2.66-2.74 (1H, m), 2.50-2.65 (2H, m), 2.08 (1H, t, J=13.3 Hz), 1.82-1.93 (1H, m, J=13.2 Hz), 1.75-1.82 (1H, m), 1.59-1.74 (2H, m); LC/MS, $t_r$=3.77 minutes (5 to 95% acetonitrile/water over 5 minutes at 1 ml/min, at 254 nm, at 50° C.).

Preparation 8

(4bR,7R,8aR)-4b-benzyl-7-hydroxy-6-oxo-7-phenyl-4b,5,6,7,8,8a,9,10-octahydrophenanthrene-2-carboxylic acid

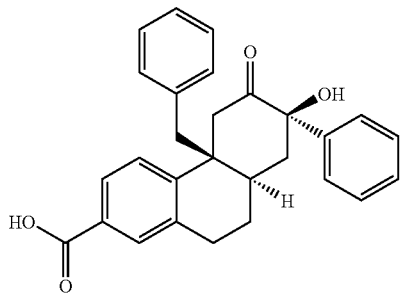

(4bR,6E,7S,8aR)-4b-benzyl-6-benzylidene-7-hydroxy-7-phenyl-4b,5,6,7,8,8a,9,10-octahydrophenanthrene-2-carboxylic acid (37.7 grams, 75.7 mmol) was dissolved in 1200 mL of methylene chloride. The reaction was cooled to −78° C. and nitrogen bubbled through the reaction mixture for 15 minutes. Next ozone was bubbled through the mixture and a blueish tinge appeared. The ozone was continuously bubble through the reaction for 3 Hours. HPLC/MS obtained at 1 hour and starting material remained. Ozone charge continued. HPLC/MS obtained at 2 hours HPLC/MS obtained at 1 hour and starting material remained. Ozone charge continued. HPLC/MS obtained at 3 hours. The consumption of starting material did not change. The ozone was stopped and nitrogen was bubbled through the reaction until the blue color dissipated. Dimethylsulfide (20 mL) and methanol (20 mL) was added and the reaction warmed to room temperature. The solvent was removed at reduced pressure and the resulting thick oil dissolved in ethyl acetate (100 mL). Heptanes (100 mL) was added to the solution and the mixture swirled. The resulting solution was slightly cloudy. The solution was stored are room temperature overnight without mixing. White crystals formed. 5.7 grams of the crystals were collected HPLC/MS and 1H NMR were obtained. The solvent was removed from the mother liquors. 44 grams of a orange brown oil was obtained. HPLC/MS obtained. The mother liquor was purified utilizing preparative reverse phase chromatography to afford an additional 22 g of the title compound for a total recovery of 27.5 g in 85% yield. MH$^+$[m/z] 501 M+Na [m/z] 523; 1H NMR (400 MHz, DMSO-$d_6$) 8 ppm 2.00 (s, 4H) 2.10-2.21 (m, 3H) 2.51 (q, 3H) 2.73-2.85 (m, 4H) 2.96-3.10

(m, 3H) 6.15 (dd, 1H) 6.60 (dd, 2H) 7.09-7.15 (m, 3H) 7.25 (d, 1H) 7.30 (d, 1H) 7.34-7.40 (m, 4H) 7.69 (s, 1H).

Preparation 9

(4bR,7R,8aR)-4b-benzyl-7-hydroxy-N-(2-methylpyridin-3-yl)-6-oxo-7-phenyl-4b,5,6,7,8,8a,9,10-octahydrophenanthrene-2-carboxamide

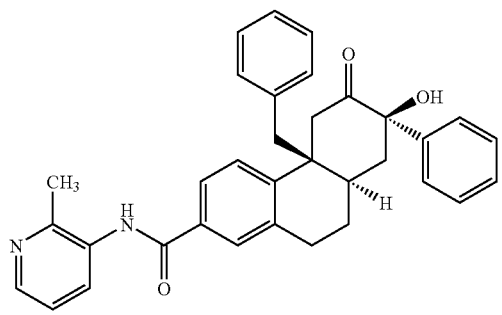

(4bR,7R,8aR)-4b-benzyl-7-hydroxy-6-oxo-7-phenyl-4b,5,6,7,8,8a,9,10-octahydrophenanthrene-2-carboxylic acid (21 g, 49.2 mmol), 3-amino-2-picoline (5.8 g, 52.2 mmol) and 1-methylimidazole (20 mL, 246.2 mmol) were dissolved in anhydrous acetonitrile (105 mL). 1-Propanephosphonic acid cyclic anhydride (50 wt % in ethyl acetate) (47 mL, 78.8 mmol) was slowly added to control the mild exotherm. The mixture was stirred at 25° C. until the reaction was completed (less than an hour). Ethyl acetate (86 mL) was added to the mixture. The mixture was washed with water (4×100 mL). The organic phase was dried with $MgSO_4$ and concentrated to dryness. The title product (22.3 g, 89% yield) was obtained as a light-yellow foam. $^1$H NMR (DMSO): δ 1.95 (m, 2H), 2.10 (m, 3H), 2.35 (s, 3H), 2.75 (m, 3H), 3.0 (d, 1H), 3.05 (m, 2H), 5.70 (s, 1H), 6.15 (d, 1H), 6.60 (m, 2H), 7.10 (m, 3H), 7.25 (m, 2H), 7.30 (m, 5H), 7.65 (d, Preparation 10

(4bR,6R,7R,8aR)-4b-benzyl-6,7-dihydroxy-6-methyl-N-(2-methylpyridin-3-yl)-7-phenyl-4b,5,6,7,8,8a,9,10-octahydrophenanthrene-2-carboxamide

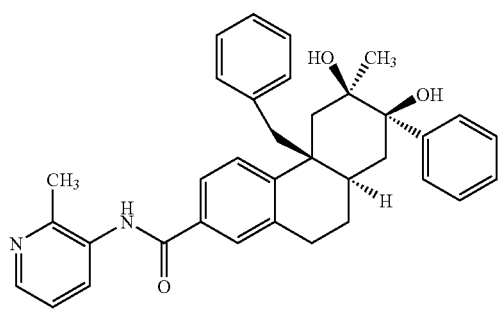

To a flame dried 50 mL round bottom flask was added the (4bR,7R,8aR)-4b-benzyl-7-hydroxy-N-(2-methylpyridin-3-yl)-6-oxo-7-phenyl-4b,5,6,7,8,8a,9,10-octahydrophenanthrene-2-carboxamide (0.28 g, 0.54 mmol) in a THF (5 mL). The solution was cooled to −17° C. in an ice/acetone bath. To the reaction was added MeLi*LiBr (0.1 mL). After 1 hour the LCMS indicated that starting material remained so an additional 0.15 mL was added. The reaction stirred to room temperature over 2 hours. By HPLC, 2.5% of the starting material remained. To the reaction was added $NH_4Cl$ slowly and off gassing was observed. The reaction was diluted to 125 mL with acetonitrile and water. The reaction was purified by reverse phase chromatography then was lyophilized. The resulting dried powder was dissolved in acetonitrile and water again with two drops of concentrated HCl. The solution was lyophilized to dryness. This afforded the title product (231.4 mg) as the HCl salt in 73% yield. LRMS $ES^+$ 533.1 1H NMR (300 MHz, METHANOL-$d_4$) δ ppm 1.23-1.28 (m, 3H) 1.53-1.62 (m, 1H) 1.90-2.20 (m, 3H) 2.70-2.74 (m, 3H) J=8.26 Hz, 2H) 6.84-6.92 (m, 2H) 6.99-7.10 (m, 3H) 7.13-7.29 (m, 3H) 7.45 (dd, J=8.15, 1.91 Hz, 1 H) 7.56-7.65 (m, 2H) 7.77 (d, J=1.81 Hz, 1H) 7.88 (dd, J=8.26, 5.84 Hz, 1H) 8.51-8.63 (m, 2H).

Example 1

(4bR,6R,7R,8aS)-4b-benzyl-6,7-dihydroxy-6-methyl-N-(2-methylpyridin-3-yl)-10-oxo-7-phenyl-4b,5,6,7,8,8a,9,10-octahydrophenanthrene-2-carboxamide

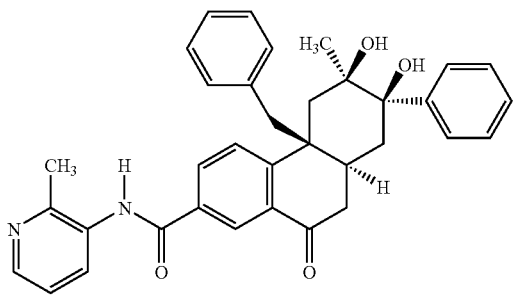

A sample of solid (4bR,6R,7R,8aR)-4b-benzyl-6,7-dihydroxy-6-methyl-N-(2-methylpyridin-3-yl)-7-phenyl-4b,5,6,7,8,8a,9,10-octahydrophenanthrene-2-carboxamide (2200 mg, 4.130 mmol) was dissolved at room temperature solution in methylene chloride (10 mL) and methanol (100 mL). This resulting solution was treated with a 10 mL solution of 2 N HCl in MeOH and was stirred for an additional 10 minutes. The reaction solution was visually inspected at this time to ensure that all solids were dissolved and then was cooled to −78° C. The cooled solution was treated with a steady stream of ozone (5 cc flow rate, generated using a Azcozon generator, AZCO Industries Ltd., model # RMU16-8 with $O_2$ pressure set to 30 psi). After five hours of constant ozone flow, the reaction was nearly complete to desired title compound by LCMS analysis (M+H LRMS 547.2 amu). The solution had taken on a deep blue color. The cold reaction solution was flushed with nitrogen for 5 minutes to dissipate most of the ozone and the reaction took on a significantly less blue color. At this time, 20 mL of dimethyl sulfide was added in a manner that did not raise the internal reaction temperature above −70 C. This was followed by removal of the cooling bath and the reaction was allowed to warm on its own accord to room temperature (1 hour), and was maintained at this temperature for 3 hours additional. At this time, the reaction solution was concentrated to a residue and dissolved in 25 mL of THF, and then the resulting THF solution was directly subjected to C-18 reverse phase chromatography (15 minute gradient run, 5% acetonitrile mobile phase to 95% acetonitrile mobile phase and water). The resulting title compound was filtered through an exchange resin (StratoSphere SPE, PL-HCO3 MP-Resin, product number 3540-C603) to remove any TFA salts and provide the title product as its parent compound. The resulting solid was crystallized by the following procedure: The solid was slurried with MeOH (7 mL), the solids collected after 1 hour and washed with an additional 2 mL of MeOH to furnish the title compound 1802 mg, 79%. Analytical data as follows: $^1$H NMR (500 MHz, $D_6$ DMSO) δ ppm 1.18 (s, 3H) 1.51 (dd, J=12.66, 1.96 Hz, 1H) 1.99 (d, J=14.96 Hz, 1H) 2.40 (dd, J=18.88, 4.85 Hz, 1H) 2.43-2.49 (m, 1H) 2.49 (br. s, 3H) 2.56 (t, J=12.82 Hz, 1H) 2.61 (d, J=12.53 Hz, 1H) 2.75 (d, J=15.12 Hz, 1H) 2.92 (dd, J=18.59, 12.74 Hz, 1H) 4.05 (d, J=12.45 Hz, 1H) 6.65 (d, J=8.27 Hz, 1H) 6.79 (dd, J=7.69, 1.59 Hz, 2H) 7.05-7.13 (m, 3H) 7.15-7.21 (m, 1H) 7.25 (t, J=7.69 Hz, 2H) 7.49 (dd, J=7.94, 5.10 Hz, 1H) 7.62 (dd, J=7.44, 1.25 Hz, 2H) 7.87 (dd, J=8.23, 2.13 Hz, 1H) 8.01 (dd, J=7.78, 1.00 Hz, 1H) 8.46 (dd, J=5.01, 1.50 Hz, 1H) 8.54 (d, J=2.09 Hz, 1H) 10.18-10.58 (m, 1H, NH). Dependant upon the water content of DMSO, two OH protons can be visible at 4.78 and 5.44 ppm. HRMS m/z 547.2619 ($C_{35}H_{35}N_2O_4$: calcd for M+H, 547.2591).

I. Biological Data

Lipopolysaccharide (LPS)-Induced Human Whole Blood

Venous blood from human donors was collected as 10 ml aliquots in tubes containing sodium heparin (BD Vacutainer from Becton Dickinson and Company, Franklin Lakes, N.Y.). Blood was added to sterile polystyrene round bottom 96-well tissue culture plates (Corning Costar) at 180 µl/well. Blood was placed in a humidified 37 C incubator with 5% $CO_2$ while compounds were prepared (nearly 60 minutes).

Compounds were prepared from 10 mM stock solutions in dimethylsulfoxide (DMSO, Sigma-Aldrich). Stock compound was diluted in DMSO to give appropriate starting concentration then diluted serially 1/3 in DMSO (i.e. 15 µl compound+30 µl DMSO), followed by diluting each serial dilution 1/167 into vehicle solution (2% DMSO in phosphate buffered saline (Dulbecco's Phosphate Buffered Saline without calcium chloride without magnesium chloride, Invitrogen Corporation, Carlsbad Calif.)). Compound or vehicle was added to blood in 10 µl aliquots as triplicates, omitting the outside wells to minimize possible edge effects. The final highest concentration of each compound in the assay ranged from 3 to 0.3 µM. Final DMSO concentration in the assay was 0.1%. The plate containing the samples was gently vortexed to mix and replaced in the incubator. LPS stock (*E. coli* serotype 0111:B4, Sigma-Aldrich), stored in aliquots of 100 µg/ml in RPMI at ~20° C., was diluted 1/50 in RPMI to make a working stock solution. After 60 minutes of incubation, 10 µl of the prepared LPS working stock was added to the blood to a final concentration of 100 µg/ml. Wells to be used as negative control received RPMI media with no LPS. The plate was again gently vortexed and the plates incubated overnight for 22 hours. Following incubation, the blood was centrifuged at 1500×g for 5 minutes and the plasma removed to either freeze at ~20° C. or assay for cytokine release.

Measurement and Analysis of Cytokine Release

IL-1β, IFN-γ and TNFα protein levels were measured using Meso Scale assay kits (Meso Scale Discovery, Gaithersburg, Md., U.S.A.). Reagents were allowed to come to room temperature. Meso Scale plates were blocked with 150 µl of Meso Scale Block B diluent, gently shaking at room temperature for 60 minutes. Plates were washed 3× with wash buffer (PBS, Invitrogen Corporation, with 0.05% Tween-20, Sigma-Aldrich). Calibrators for standard curves were prepared in human plasma/serum assay diluent as a 1/5 serial dilution to achieve final concentrations ranging from 50000 pg/ml to 3.2 pg/ml. Samples were added at 10 to 20 µl/well and calibrators were added at 20 µl/well, then incubated at room temperature with gentle shaking for 2 hours. Plates were again washed 3× with wash buffer. Detection antibody was diluted in human plasma/serum antibody diluent to 1 µg/ml and added to the plate at 20 µl/well. Plates were incubated as before for 2 hours and washed again. Read Buffer T (4×) was diluted 1:1 with mq$H_2O$ to 2× concentration and 150 µl added to each well. Plates were read on the SECTOR Imager 6000 (Meso Scale Discovery) to generate raw signal values.

Individual sample signal values were compared to positive and negative controls (vehicle treated blood with LPS and vehicle treated blood without LPS, respectively) to generate % inhibition. Triplicate values were averaged for each donor. The values for three or four donors were averaged and graphed using 4-parameter fit curves in the LabStats plug-in for the Microsoft Excel application.

Prednisolone was obtained from Sigma-Aldrich (Saint Louis, Mo.).

TABLE 1

Mean Values of Prednisolone Inhibition

| Concentration (nM) | IFNγ (% inhibition) | TNFα (% inhibition) | IL-1β (% inhibition) |
|---|---|---|---|
| 1000 | 96.41887 | 90.42849 | 91.81285 |
| 333.3333 | 94.80171 | 86.9239 | 87.6417 |
| 111.1111 | 85.21585 | 67.08184 | 61.87842 |
| 37.03704 | 70.72071 | 49.23688 | 36.70005 |
| 12.34568 | 34.71695 | 19.56738 | 7.168145 |
| 4.115226 | 25.24299 | 8.949503 | 0.83998 |
| 1.371742 | 9.7537 | 6.36281 | −1.2607 |
| 0.457247 | 1.188799 | 2.756104 | −0.57073 |

TABLE 2

Mean Values of Example 1 Inhibition

| Concentration (nM) | IFNγ (% inhibition) | TNFα (% inhibition) | IL-1β (% inhibition) |
|---|---|---|---|
| 300 | 72.90548 | 42.80632 | 38.01507 |
| 100 | 72.50547 | 42.18648 | 37.61988 |
| 33.33333 | 66.18697 | 30.67716 | 26.41755 |
| 11.11111 | 50.99181 | 18.11116 | 15.35196 |
| 3.703704 | 26.94135 | 7.08568 | 5.139857 |
| 1.234568 | 18.37372 | 0.8113 | 1.175317 |
| 0.411523 | 15.63071 | −3.618 | −1.0797 |
| 0.137174 | −3.92851 | 0.604014 | −0.93988 |

Comparator A is (4βS,7S,8αR)-4β-benzyl-7-hydroxy-N-((2-methylpyridin-3-yl)methyl)-7-(3,3,3-trifluoropropyl)-4β,5,6,7,8,8α,9,10-octahydrophenanthrene-2-carboxamide, the synthesis for which is described as Example No. 771C-3 on page 241 of WO 00/66522 (Dow et al.), and has the following structure:

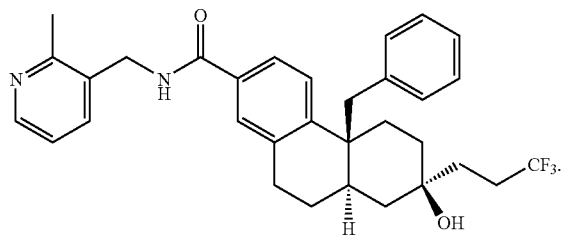

The following comparative compounds, Comparators B, C and D, can be prepared by methods described herein, those known in the art and Scheme D, below.

Comparator B

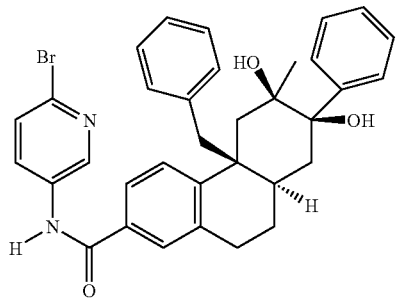

(4bR,6R,7R,8aR)-4b-benzyl-N-(6-bromo-2-methylpyridin-3-yl)-6,7-dihydroxy-6-methyl-7-phenyl-4b,5,6,7,8,8a,9,10-octahydrophenanthrene-2-carboxamide Comparator C

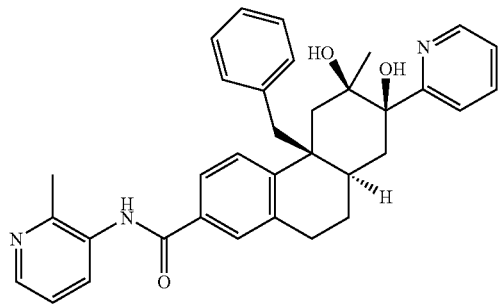

(4bR,6R,7R,8aR)-4b-benzyl-6,7-dihydroxy-6-methyl-N-(2-methylpyridin-3-yl)-7-(pyridin-2-yl)-4b,5,6,7,8,8a,9,10-octahydrophenanthrene-2-carboxamide Comparator D

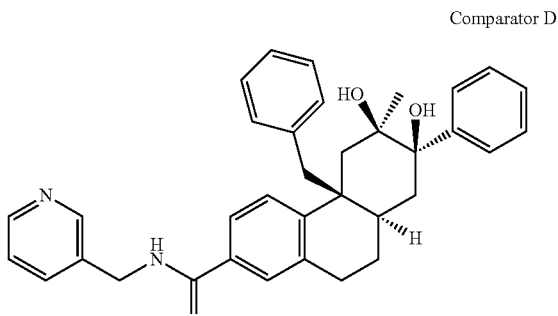

(4bR,6R,7R,8aR)-4b-benzyl-6,7-dihydroxy-6-methyl-7-phenyl-N-(pyridin-3-ylmethyl)-4b,5,6,7,8,8a,9,10-octahydrophenanthrene-2-carboxamide Scheme D

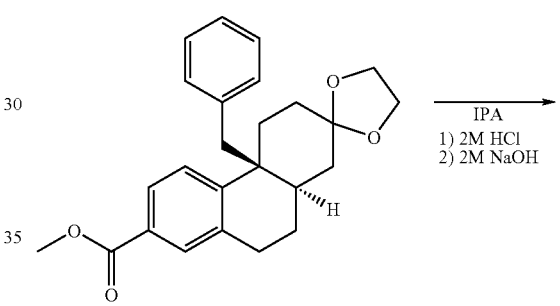

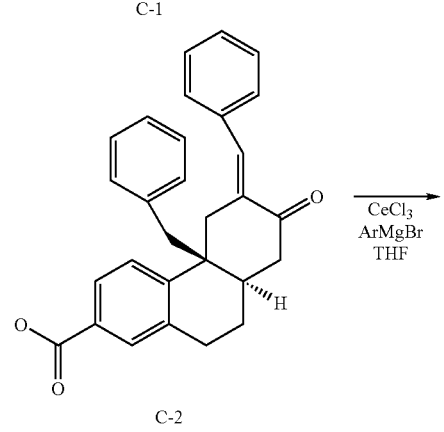

-continued
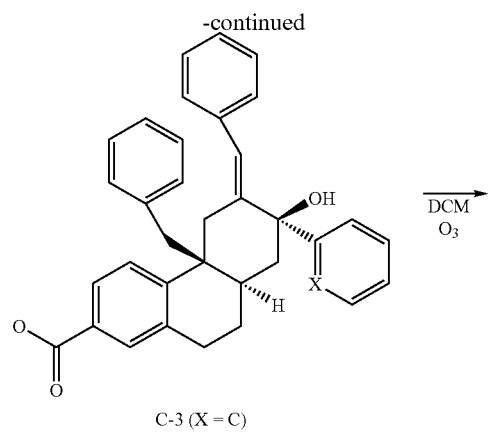
C-3 (X = C)
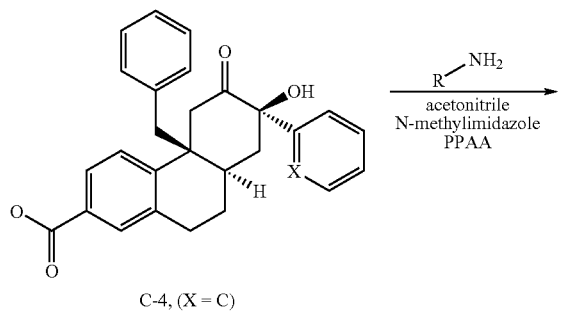
C-4, (X = C)
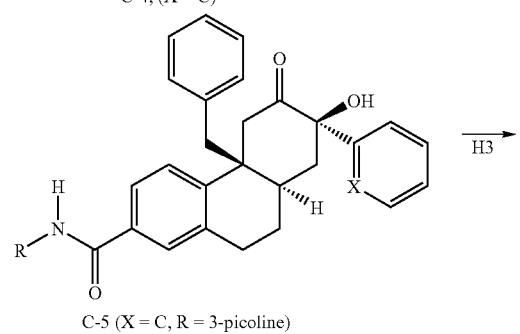
C-5 (X = C, R = 3-picoline)
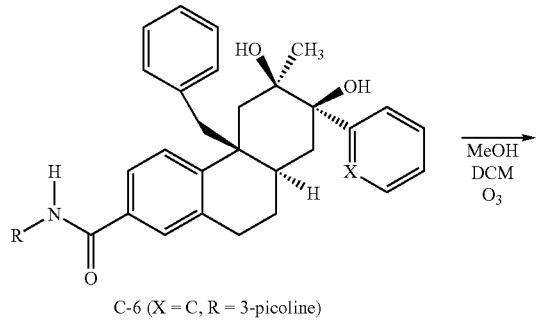
C-6 (X = C, R = 3-picoline)
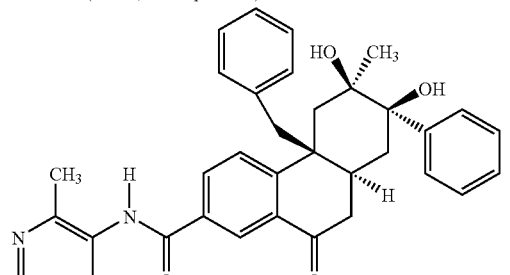
C-7
The following comparative compound, Comparator E, can be prepared by general methods known in the art and Reaction Scheme E, below.
Comparator E
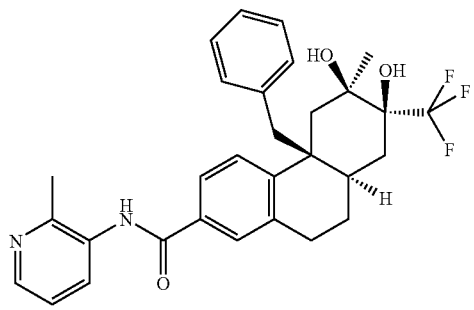
(4bR,6R,7S,8aR)-4b-benzyl-6,7-dihydroxy-6-methyl-N-(2-methylpyridin-3-yl)-7-(trifluoromethyl)-4b,5,6,7,8,8a,9,10-octahydrophenanthrene-2-carboxamide
Scheme E
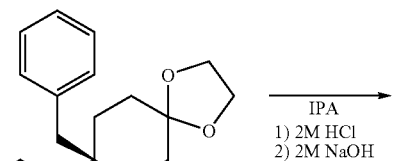
B-4
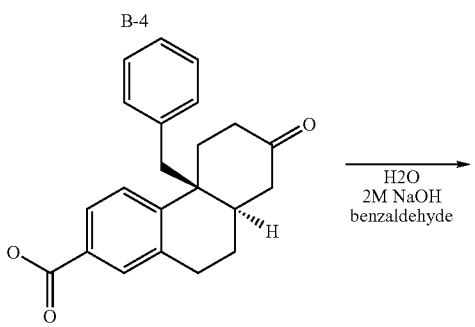
C-1
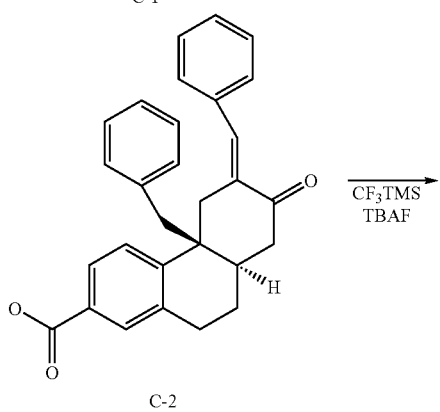
C-2

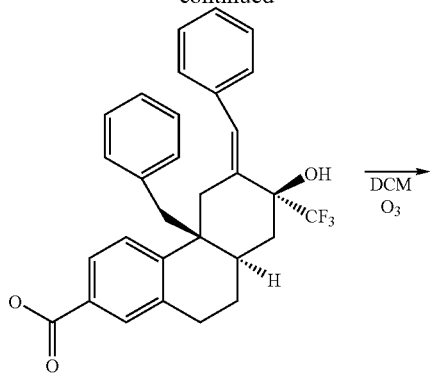
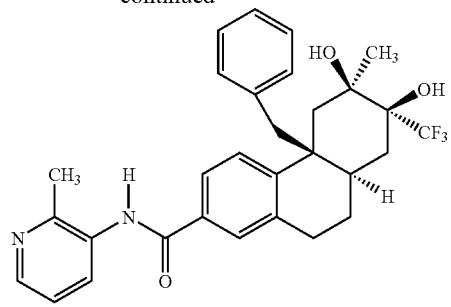

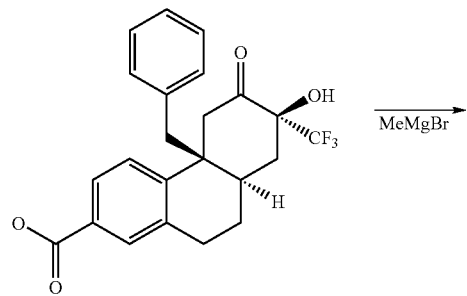
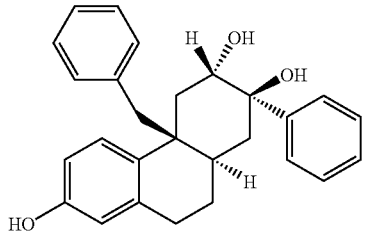

Comparator F is (2R,3S,4aR,10aR)-4a-Benzyl-2-phenyl-1,2,3,4,4a,9,10,10a-octahydrophenanthrene-2,3,7-triol, the synthesis of which is described as Example 30 on page 106 of international application WO 2004/005229 (Chantigny et al.) and has the following structure:

ABS

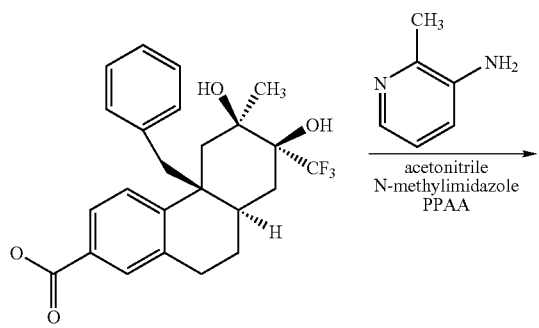
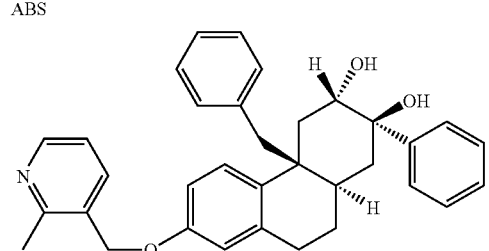

Comparator G is (2R,3S,4aR,10aR)-4a-Benzyl-7(2-methylpyridin-3-ylmethoxy)-2-phenyl-1,2,3,4,4a,9,10,10a-octahydrophenanthrene-2,3 diol, the synthesis of which is described as Example 32 on page 107 of international application WO 2004/005229 (Chantigny et al.) and has the following structure:

ABS

TABLE 3

| Mean Values of Comparator A Inhibition | | | | |
|---|---|---|---|---|
| Concentration (nM) | IFNγ (% inhibition) | TNFα (% inhibition) | IL-1β (% inhibition) | IL-6 (% inhibition) |
| 3000 | 28.02163 | −3.03631 | 16.37219 | −1.97032 |
| 1000 | 16.52981 | −5.43701 | 14.96801 | −0.88954 |
| 333.3333 | −6.31952 | −4.61436 | 12.23526 | −2.8341 |
| 111.1111 | 8.737671 | −3.82374 | 8.59594 | −3.49518 |
| 37.03704 | −9.80677 | −4.19291 | 17.27236 | −3.52461 |
| 12.34568 | 0.016012 | 0.030908 | 22.84851 | −1.12581 |
| 4.115226 | −1.69672 | −0.86051 | 22.01534 | −4.3436 |
| 1.371742 | 18.09167 | 18.1316 | 31.97474 | 1.459164 |

TABLE 4

Mean Values of Comparator F Inhibition

| Concentration (nM) | IFNγ (% inhibition) | TNFα (% inhibition) | IL-1β (% inhibition) |
|---|---|---|---|
| 3000 | 21.95778 | 3.808591 | 3.308508 |
| 1000 | 14.6234 | 4.138398 | 0.21981 |
| 333.3333 | −3.30077 | −3.43225 | −2.45189 |
| 111.1111 | −4.60435 | −6.35337 | −4.59067 |
| 37.03704 | −13.3589 | −4.22595 | −6.15082 |
| 12.34568 | −8.35374 | −6.79409 | −5.49194 |
| 4.115226 | −15.284 | −8.12294 | −6.1571 |
| 1.371742 | −12.4462 | −2.51053 | −4.16143 |

TABLE 5

Mean Values of Comparator G Inhibition

| Concentration (nM) | IFNγ (% inhibition) | TNFα (% inhibition) | IL-1β (% inhibition) |
|---|---|---|---|
| 3000 | 41.3796 | 16.28448 | 15.47551 |
| 1000 | 13.20202 | −8.47459 | −1.19319 |
| 333.3333 | 2.019883 | −13.7986 | −6.75215 |
| 111.1111 | 2.655063 | −8.76041 | −5.37397 |
| 37.03704 | −2.5794 | −13.8733 | −7.35195 |
| 12.34568 | −9.15435 | −14.0438 | −7.52021 |
| 4.115226 | 12.82205 | −2.89901 | −2.63902 |
| 1.371742 | 16.69609 | 3.216606 | −0.11505 |

Example 1, Comparator F, Comparator G and prednisolone are all ligands of the glucocorticoid receptor, however, each one confers a distinct profile in the inhibition of cytokines from ex vivo LPS-stimulated human whole blood. Prednisolone, a full agonist of GR, demonstrates full inhibition of IFN□, TNF□ and IL-1□. Example 1 also inhibits cytokine release in a concentration-dependent manner. Being a partial agonist/antagonist, Example 1 does not show inhibition to the extent of prednisolone. Furthermore, the level of inhibition observed for Example 1 is different between cytokines measured, that is to say, IFN□=73%, TNF□=43%, and IL-1□=38%. In contrast to Example 1, Comparator F and Comparator G do not significantly inhibit TNF□ or IL-1□ (less than 20% at 3000 nM) and show a very much less efficacious inhibition of IFN□ (only 22% or 41% inhibition at 3000 nM, respectively). Thus, while Example 1, Comparator F, Comparator G and prednisolone bind to the same receptor, they demonstrate markedly different activities.

In Vivo Data

Mouse Collagen-induced arthritis (mCIA)

Mouse Collagen-induced arthritis is a commonly used chronic, preclinical model of rheumatoid arthritis in which joint swelling and bone destruction occur following immunization with type II collagen. Reduction of disease incidence and severity has been shown previously to be predictive of disease-modification and signs and symptoms mitigation, respectively, in a clinical setting.

In the therapeutic mCIA model, induction of disease incidence and severity was synchronized via LPS stimulation. Male DBA/J mice were immunized with 100 ug of bovine type II collagen (bCII) on day 0. All mice received an intraperitoneal injection of 20 μg of LPS on day 28 and disease was allowed to develop through day 34. At day 34, all mice had disease (incidence=100%) with an average severity score of seven. Dosing of compounds was initiated in the therapeutic mode on day 34 and continued through day 49. Different treatments were compared by measuring the decrease in incidence (i.e., resolution of disease) and the decrease in severity of paw swelling over time.

28-Day Mouse Side-Effect Model 10-12 week old female Swiss Webster mice (Taconic, Germantown, N.Y., U.S.A.) weighing 27-29 grams are used in accordance with the guidelines of the Institutional Animal Care and Use Committee and in accordance with NIH guidelines on laboratory animal welfare. Mice are acclimated to the Pfizer animal facility for 3-7 days prior to being placed on study. Prednisolone and DAGR compounds are administered by oral gavage for a total of 28 days. Each treatment group generally contains 8-10 mice. To establish a dosing regimen for the studies, a pilot pharmacodynamic time course experiment is conducted to quantify TNFa repression after a single $ED_{80}$ dose (determined from the acute LPS endotoxemia mouse model). In order to repress TNFa significantly over a 24 hour period, it was determined that prednisolone required b.i.d. dosing. DAGR compounds vary in their required frequency of doses.

Body weights are measured on the first and last day of each experiment. Blood samples are obtained after ~3 weeks of dosing for steady-state pharmacokinetic analysis. To assess compound effects on LPS-induced TNF-a, all mice receive an intraperitoneal injection of LPS (*Salmonella Typhosa*, Sigma, St. Louis, L-7895) 2.5 hr after the last dose on day 28. Mice are sacrificed 90 min. after LPS administration. Serum samples are assayed for osteocalcin and TNFa using the Linco multiplex assay (St. Charles, Mo.) and Luminex 100 (Austin, Tex.). Samples are diluted 1:20 and the assay is run according to manufacturer's instructions. An osteocalcin standard is purchased separately from Biomedical Technologies Incorporated (Stoughton, Mass.). Serum insulin is measured to assess compound effects on insulin resistance. Insulin was measured using the UltraSensitive Mouse EIA kit from Alpco Diagnostics (Salem, N.H.) following the manufacturer's protocol.

Cortical Bone Histomorphometry

During the in-life portion of each study, mice received two IP injections of the fluorochrome calcein (C-0875; Sigma-Aldrich; 20 mg/kg; 200 μL/mouse), dissolved in 2% sodium bicarbonate, on days 1 and 26 for bone histomorphometry measurements. Fluorochrome labels incorporate into the bone mineral and allow measurement of bone formation rate. During the tissue harvest, the left tibia is excised and cleaned for cortical histomorphometry measurements. After all skin and muscle are removed, tibiae are placed in 70% ethanol (4° C.) in the dark for a minimum of 24 hours.

Ground transverse sections are used for histomorphometric analysis of cortical bone'. Bones are sectioned using a low speed saw (Isomet, Buehler, Lake Bluff, Ill.) equipped with a diamond wafer blade. The end of each tibia is removed proximal to tibia-fibula synostosis and a 75 mm cross-section is cut. Using a roughened glass plate and a cork, sections are ground to ~25 mm until transparent and all labels distinguishable under a fluorescent microscope. Sections are dehydrated using the following solutions for a minimum of 2 minutes each: 1) 70% ethanol, 2) 95% ethanol, 3) 100% ethanol, 4) 50/50 ethanol/xylene, and 5) xylene (twice) (Sigma, St.

Louis, 534056). Sections are mounted using Eukitt Quick-Mounting Medium (Sigma, St. Louis, 03989) and cover-slipped. Using the Osteomeasure Bone Analysis Program (Decatur, Ga.), bone formation rate is calculated by tracing the $1^{st}$ and $2^{nd}$ fluorescent labels in addition to tracing the inner and outer perimeter of the bone. Bone formation rate is calculated by the following equation: (Interlabel Width/Label Interval)*(Labeled Perimeter/Bone Perimeter). At least 5 samples are measured from each treatment group in each study.

Standard and Sample Preparation for PK Analysis and the LC/MS/MS System

Corticosterone, prednisolone, and compound levels are measured in all serum samples. The following standards are prepared in control mouse serum from a stock in DMSO: 5, 2.5, 1.25, 0.3125, 0.078, 0.0195, 0.00488, 0.00122, 0.00305, 0.000076 μg/mL. 30 μL of serum samples (unknown samples and std serum samples) are transferred to a new 96-vial plate. Acetonitrile (170 ml, containing 1 μM tolbutamide as internal std) is added to precipitate the serum and provide the internal standard for MS/MS analysis. The plate is centrifuged for 5 min at 4000 rpm, 25° C. Ninety μL of supernatant is transferred for injection and 5 μL was injected in the LC/MS/MS system for analysis. Concentrations below the limit of quantitation (LOQ) are reported as zero (0) and are used in the evaluation of mean concentrations and the estimation of AUC. The area under the concentration-time curve from time zero to time of the last quantifiable concentration (t) [AUC (0-t)] is determined using the linear trapezoidal method.

Statistical Evaluation $ED_{50}$ and $ED_{80}$ values are obtained for the various parameters using four-parameter logistic fits of data. For each experiment/dose group, outliers are detected by calculating the number of standard deviations each mouse's value was from the mean of their group and then dividing by the standard deviation of the group. The means and standard deviations used in this calculation omitted the value being examined so that, if it were an outlier, it would have no influence. If the value being examined is more than 2.5 standard deviations from the mean, it was not used in the rest of the calculations.

Percent inhibition values are then calculated for each animal using the means of the vehicle and 10 mpk prednisone control groups. The individual mouse percent inhibition values are then fit to a four-parameter logistic model using the area under curve mean for each group. Since all four parameters are estimated and the lower plateau is not fixed at 0% and the upper plateau was not fixed at 100%, the $ED_{50}$ and $ED_{80}$ values are calculated by using an inverse calibration formula for a response equal to 50% or 80%. The designation "nd" means not determined.

| Compound Name | Therapeutic mCIA ($ED_{50}$ dose) | Therapeutic mCIA ($ED_{80}$ dose) | TNFα Suppression ($ED_{50}$ dose) | TNFα Suppression ($ED_{80}$ dose) | Osteocalcin Suppression ($ED_{50}$ dose) | Osteocalcin Suppression ($ED_{80}$ dose) |
|---|---|---|---|---|---|---|
| Example 1 | 0.3 | 1.61 | 0.029 | 0.11 | 0.081 | 0.35 |
| Comparator B | nd | nd | 0.083 | 0.45 | 0.21 | 0.97 |
| Comparator C | 0.8 | 2.9 | 3.08 | 9.87 | 3.68 | >20 |
| Comparator D | nd | nd | 11.40 | 14.48 | >60 | >60 |
| Comparator E | 0.13 | 1.15 | >1 | >1 | 0.78 | >1 |

| Compound Name | BFR ($ED_{50}$ dose) | BFR ($ED_{80}$ dose) | Insulin ($ED_{50}$ dose) | Insulin ($ED_{80}$ dose) |
|---|---|---|---|---|
| Example 1 | 0.12 | 0.87 | 1.28 | 5.89 |
| Comparator B | nd | nd | 1.04 | 7.58 |
| Comparator C | 3.72 | 7.88 | >20 | >20 |
| Comparator D | 35.86 | >60 | >60 | >60 |
| Comparator E | 0.28 | 0.33 | >1 | >1 |

Dissociation Index

A dissociation index (DI) was chosen as a measurement to quantify the dissociation of compounds relative to that of prednisolone in terms of biomarkers of anti-inflammatory efficacy and side-effects. Dissociation indices were calculated using clinically relevant biomarkers that could be utilized in early clinical development. Serum osteocalcin and LPS-induced serum TNFα are accepted clinically as predictive for bone formation and anti-inflammatory efficacy, respectively.

The dissociation index was based on the following tenets:

1) Dissociation required a dose-margin between biomarkers of inflammation and side-effects [such as osteocalcin (OC), insulin, or bone formation rate], and was defined by the formula, using osteocalcin suppression (OC) as the side effect example:

$$DI = \frac{\text{Side-effect endpoint}}{\text{Anti-inflammatory endpoint}}$$

For example:

$$DI = \frac{\text{osteocalcin suppression } (OC)ED_{50}(\text{or } EAUC_{50})}{TNF\alpha \text{ supprepression } (TNF\alpha ED_{50}(\text{or } EAUC_{50})}.$$

2) The DI of a compound can be considered relative to that observed with prednisolone, its clinical comparator. The corrected or normalized DI was defined as compound DI divided by prednisolone DI.

| Dissociation Index | | | | | | |
|---|---|---|---|---|---|---|
| Compound Name | OC/TNF ($ED_{50}$ dose) | OC/TNF ($ED_{80}$ dose) | BFR/TNF ($ED_{50}$ dose) | BFR/TNF ($ED_{80}$ dose) | Insulin/TNF ($ED_{50}$ dose) | Insulin/TNF ($ED_{80}$ dose) |
| Example 1 | 2.8 | 3.2 | 4.1 | 7.9 | 44.1 | 5.5 |
| Comparator B | 2.5 | 2.2 | nd | nd | 12.5 | 16.8 |
| Comparator C | 1.2 | >2 | 1.2 | 0.8 | >6.5 | >2 |
| Comparator D | >5.3 | >4.1 | 3.1 | >4.1 | >5.3 | >4.1 |
| Comparator E | <0.8 | <1 | <0.3 | <0.3 | Cannot Calculate | Cannot Calculate |

| Corrected Dissociation Index | | | | | | |
|---|---|---|---|---|---|---|
| Compound Name | OC/TNF ($ED_{50}$ dose) | OC/TNF ($ED_{80}$ dose) | BFR/TNF ($ED_{50}$ dose) | BFR/TNF ($ED_{80}$ dose) | Insulin/TNF ($ED_{50}$ dose) | Insulin/TNF ($ED_{80}$ dose) |
| Example 1 | 3.1 | 1.6 | 5.1 | 6.1 | 4.8 | 11.1 |
| Comparator B | 2.8 | 1.1 | nd | nd | 1.4 | 3.5 |
| Comparator C | 1.3 | >2 | 1.5 | 0.6 | >0.7 | >0.4 |
| Comparator D | >5.9 | >2.1 | 3.9 | >3.2 | >0.6 | >0.9 |
| Comparator E | <0.9 | <0.5 | <0.4 | <0.2 | Cannot Calculate | Cannot Calculate |

I claim:

1. A compound of Formula I:

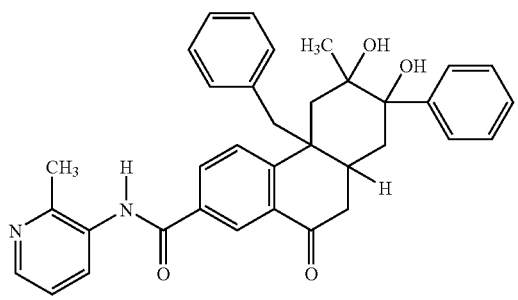

(I)

or salt thereof.

2. The compound of claim 1, wherein the compound is (4bR,6R,7R,8aS)-4b-benzyl-6,7-dihydroxy-6-methyl-N-(2-methylpyridin-3-yl)-10-oxo-7-phenyl-4b,5,6,7,8,8a,9,10-octahydrophenanthrene-2-carboxamide; or a pharmaceutically acceptable salt thereof.

3. The calcium salt of the compound of claim 2.

4. The sodium salt of the compound of claim 2.

5. A composition comprising the compound of claim 1 or salt thereof and a pharmaceutically acceptable carrier.

6. The composition of claim 5, comprising a pharmaceutically effective amount of (4bR,6R,7R,8aS)-4b-benzyl-6,7-dihydroxy-6-methyl-N-(2-methylpyridin-3-yl)-10-oxo-7-phenyl-4b,5,6,7,8,8a,9,10-octahydrophenanthrene-2-carboxamide, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO.       : 8,148,409 B2                              Page 1 of 1
APPLICATION NO.  : 12/505932
DATED            : April 3, 2012
INVENTOR(S)      : Paul V. Rucker It is certified that error appears in the above-identified patent and that said Letters Patent is hereby corrected as shown below:

On title page item (54) and col. 1, lines 1-2: Please change "PHENATHERENON COMPOUNDS COMPOSITONS AND METHODS" to --PHENANTHRENONE COMPOUNDS, COMPOSITIONS AND METHODS--.

Signed and Sealed this
Fourteenth Day of August, 2012

David J. Kappos
*Director of the United States Patent and Trademark Office*